(12) United States Patent
Ratcliffe et al.

(10) Patent No.: US 6,787,326 B1
(45) Date of Patent: Sep. 7, 2004

US006787326B1

(54) INTERACTION BETWEEN THE VHL TUMOR SUPPRESSOR AND HYPOXIA INDUCIBLE FACTOR, AND ASSAY METHODS RELATING THERETO

(75) Inventors: Peter John Ratcliffe, Oxford (GB); Patrick Henry Maxwell, Oxford (GB); Christopher William Pugh, Oxford (GB)

(73) Assignee: ISIS Innovation Limited, Oxford (GB)

( * ) Notice: Subject to any disclaimer, the term of this patent is extended or adjusted under 35 U.S.C. 154(b) by 0 days.

(21) Appl. No.: 09/959,873

(22) PCT Filed: May 12, 2000

(86) PCT No.: PCT/GB00/01826

§ 371 (c)(1),
(2), (4) Date: Nov. 9, 2001

(87) PCT Pub. No.: WO00/69908

PCT Pub. Date: Nov. 23, 2000

(30) Foreign Application Priority Data

May 12, 1999 (GB) .............................................. 9911047

(51) Int. Cl.[7] ........................... C12Q 1/54; G01N 33/53
(52) U.S. Cl. .............................. 435/14; 435/6; 435/7.1; 435/8; 530/350
(58) Field of Search .............................. 435/8, 14, 4, 6, 435/7.1, 7.2, 7.31; 530/350

(56) References Cited

FOREIGN PATENT DOCUMENTS

WO        0029437        5/2000

OTHER PUBLICATIONS

Genbank accession No. AF010238 (Nov. 24, 2000).*
Latif et al (Science 1993, vol. 28, pp. 1317–1320, abstract only).*
GenBank accession No. U22431 (1995).*
*Nature* (London), vol. 339, No. 6733, pp. 271–275, (1999). Maxwell et al., "The Tumour Suppressor Protein VHL Targets Hypoxia–Inducible Factors for Oxygen–dependent Proteolysis."
*Science*, vol. 284, No. 5413, pp. 455–461, (1999). Stebbins et al., Structure of the VHL ElonginC–ElonginB Complex: Implications for VHL Tumor Suppressor Function.
*Kidney International*, vol. 51, No. 2, pp. 575–578, (1997). Levy et al., "Regulation of Vascular Endothelial Growth Factor by Hypoxia and its Modulation by the von Hippel-Lindau Tumor Suppressor Gene."
*J. Bio. Chem.*, vol. 272, No. 17, pp. 11205–11214, (1997). Pugh et al., "Activation of Hypoxia–Inducible Factor–1 Definition of Regulatory Domains within the Alpha Subunit."
*J. Bio. Chem.*, vol. 272, No. 31, pp. 19253–19260 (1997). Jiang et al., "Transactivation and Inhibitory Domains of Hypoxia–Inducible Factor 1–alpha."
*J. Bio. Chem.*, vol. 274, No. 10, pp. 6519–6525 (1999). Kallio et al., "Regulation of the Hypoxia–Inducible Transcription Factor 1α by the ubiquitin–proteasome Pathway."
*Proc. Natl. Acad. Sci.*, vol. 94, pp. 8104–8109, (1997). Maxwell et al. "Hypoxia–inducible Factor–1 Modulates Gene Expression in Solid Tumors and Influences Both Angiogenesis and Tumor Growth."

* cited by examiner

Primary Examiner—Larry R. Helms
Assistant Examiner—Misook Yu
(74) *Attorney, Agent, or Firm*—Hamilton, Brook, Smith & Reynolds, P.C.

(57) ABSTRACT

The invention relates to the finding that the VHL tumour suppressor protein regulates hypoxia inducible factor α subunits, by targeting HIF α for destruction in normoxic, but not hypoxic cells. The invention provides assays for modulators of this interaction, and peptides based upon HIF α subunit sequence which may modulate this interaction.

16 Claims, 9 Drawing Sheets

```
              MPRRAENWDEAEVGAEEAGVEEYGPEEDGGEESGAEESGPEESG
PEELGAEEEMEAGRPRPVLRSVNSREPSQVIFCNRSPRVVLPVWLNFDGEPQPYPTLP
PGTGRRIHSYRGHLWLFRDAGTHDGLLVNQTELFVPSLNVDGQPIFANITLPVYTLKE
RCLQVVRSLVKPENYRRLDIVRSLYEDLEDHPNVQKDLERLTQERIAHQRMGD
                                                        (SEQ ID NO: 16)
```

MPRRAENWDEAEVGAEEAGVEEYGPEEDGGEESGAEESGPEESG
PEELGAEEEMEAGRPRPVLRSVNSREPSQVIFCNRSPRVVLPVWLNFDGEPQPYPTLP
PGTGRRIHSYRGHLWLFRDAGTHDGLLVNQTELFVPSLNVDGQPIFANITLPVYTLKE
RCLQVVRSLVKPENYRRLDIVRSLYEDLEDHPNVQKDLERLTQERIAHQRMGD (SEQ ID NO: 16)

FIG. 1A

```
   1 gaattcagtt agttgacttt ttgtacttta taagcgtgat gattgggtgt tcccgtgtga
  61 gatgcgccac cctcgaacct tgttacgacg tcggcacatt gcgcgtctga catgaagaaa
 121 aaaaaaattc agttagtcca ccaggcacag tggctaaggc ctgtaatccc tgcactttga
 181 gaggccaagg caggaggatc acttgaaccc aggagttcga gaccagccta ggcaacatag
 241 cgagactccg tttcaaacaa caaataaaaa taattagtcg ggcatggtgg tgcgcgccta
 301 cagtaccaac tactcgggag gctgaggcga gacgatcgct tgagccaggg aggtcaaggc
 361 tgcagtgagc caagctcgcg ccactgcact ccagcccggg cgacagagtg agaccctgtc
 421 tccaaaaaaa aaaaaaaaca ccaaacctta gaggggtgaa aaaaaatttt atagtggaaa
 481 tacagtaacg agttggccta gcctcgcctc cgttacaaca gcctacggtg ctggaggatc
 541 cttctgcgca cgcgcacagc ctccggccgg ctatttccgc gagcgcgttc catcctctac
 601 cgagcgcgcg cgaagactac ggaggtcgac tcgggagcgc gcacgcagct ccgccccgcg
 661 tccgacccgc ggatcccgcg gcgtccggcc cgggtggtct ggatcgcgga gggaatgccc
 721 cggagggcgg agaactggga cgaggccgag gtaggcgcgg aggaggcagg cgtcgaagag
 781 tacggccctg aagaagacgg cggggaggag tcgggcgccg aggagtccgg cccggaagag
 841 tccggcccgg aggaactggg cgccgaggag gagatggagg ccgggcggcc gcggcccgtg
 901 ctgcgctcgg tgaactcgcg cgagccctcc caggtcatct tctgcaatcg cagtccgcgc
 961 gtcgtgctgc ccgtatggct caacttcgac ggcgagccgc agccctaccc aacgctgccg
1021 cctggcacgg gccgccgcat ccacagctac cgaggtacgg gcccggcgct taggcccgac
1081 ccagcaggga cgatagcacg gtctgaagcc cctctaccgc cccggggtcc attttgcaga
1141 cggggaactg aggccccttg aggcaggaca catccagggt gacgctgctc gtaagcgtca
1201 gagcattctt tttttttttt tttttttttt tctgagacgg agtctcgctc tgtcgcccag
1261 gctggagtgc agtggcgcga tctcgactca ctgcagcctc cgcctcccgg gttcaagcga
1321 ttctcctgcc tcagcctcct gagtagctgg gattacaggc gtgcgccacc gcgcccggct
1381 gatttttata ttttttagtag agacggggtt tcaccatgtt ggtcaggctg gtctcgaact
1441 aactgacctc gtgatccgcc cgcctcggcc ttcccaaagt gctgggctta tgggcatgag
1501 cctccgcgcc cggcccagag cattctttat aaggccgaat agtttgcatt tgaaggtggc
1561 tcccccccag tccccaccc cacgtgtatt ttcccctcaa agaaaagctg catccttaac
1621 accccatctg ttcagtcctc atgactccag tgggccagtt ctgcgtagtc cctgccctcg
1681 tggagaacac attcctcctg gggagactga cagatgcaaa gacaggaaca agccagggtc
1741 atgttggcgc cggaagagcc gaccgtgtgt ggcgtgggaa attgacttac ctgcctgctg
1801 ggagatggag gggttgcggt tgtgtggttt cagttaagga gcacttccg gagaaggaag
1861 agagcaggat ggagtaggaa ctagccaacc ctaggtaaga ggttctagac atgcgtgcgt
1921 tgagacctgg agtcttggga gaggatgctt aaaaggtgat tttaccccta ggaatatggg
1981 ggcactgaaa ttttttttttt ttttgagac gggagtcttg ctctgcaagc tggagtgcag
2041 tggcccacgc tagaatgcag tggcgcgatt gcggctcatt gcaacatctg ccacctgggg
2101 tcaagtggtt ctcttgcctc agcctcccga ggagcgggga ttactggcgt gcgccaccac
2161 tcctggctaa ttttttttt agtagagacg ggggtttcgt catttggct aggctggtct
2221 cgaactcctg acctcagatg atccacccgc cttggcctcc caaagtgctg agattacagg
2281 tgtaagccac tgcgcccagc cctttgaaag tttttcagta tttatgtata tatattttg
2341 agttggagtc tggatctgtc gccagactgg agtgctgttg cacaatcttg gctcactgca
```

FIG. 1B

```
2401 atctccgact ccctggttca agcgattctc ctgcctcagc ctcccaagta gctgggatta
2461 caggcacgca ctaccattcc cagctaattt tttgtattct tagtagagac agggtttcac
2521 catgttggcc aggatggtct ccatctcctg cgctcgtgat ctgcctgctt cggcctccca
2581 aagtgctggg attacaggcg tgctgggatt tcggccacaa cgtccgaccg aaagttttta
2641 agcagggaca tgacattgtc agatttatat actgaaaagc tcacccaggt tgccaagtgg
2701 tttggagggg aaagactgct gtcgaggaag cagttaggta gttgtgaaaa cccaggtgag
2761 gaataactag gccttaccta aggtgcaggc agtaatcttg ccatggcctt taagcagaga
2821 agtagtccta gtgtcactta atctttacaa aggattttg caaggatccc gatctttctt
2881 ccttgagggt ggtgtactta atacactttt acaccagact tctaatgtta gatgaagaac
2941 acagtatttc cagggatcaa catttctgta ggctcctatt ttatatagga aattgtatga
3001 attttgtatt ttactccaaa attttctgt gcccgattta atataaaaat ttactgagcc
3061 tgggtgcagt ggctcatgcc tgtgatctca gcactttggg aggctgaggc aggaggattt
3121 cttgagccca ggagctggag accagcctgt gcaacatagt gagaccctgt ctgtatttaa
3181 aaaaaaaaaa aaattcttga aaaattagca gggcacattc ctgcctttag tcccagctac
3241 tgggaagct gaggcaggaa gatcacccga acccaggagt tggaggctac agtgaactat
3301 gatggtcct ctgaatagtt gctgtactct agtctggtaa cacagcaaga ccctgtctct
3361 ctatcttgtc tttttttttt ttttttttg agacaggatg tcctgctgtt gcctgggctg
3421 gagtgtggag gctgagttt ggtggcatga tcacggctca ttgcacctt aacctgggct
3481 caagcagtcc tcccagagct tcagcttccc aaagtagctg ggactatagg catgctccac
3541 tatgtctggc taatttcttt ttttatttt atttttagta gagatgaggt cttgctatgt
3601 tgcccaggct gagacctcat ctcttttta tttttttaa atttttatt atactttaag
3661 ttctagggta catgtgcaca acgtgcaggt ttgttacata tgtaaacatg tgccatgttg
3721 gtgtgctgca cccatagaga cctcgtctta aaaaagaaa ataacattac ttttgaaggt
3781 acttaatgca ctgaattgta catttaaaaa tggttaaaat ggtaaatgtt tgaggcaggt
3841 agatccacct gaggtcagga gttcaagacc agcctgacca atatggtgga accctgtctc
3901 tgctaaaaat acaaaagtta gctgcatgtg gtggcatgcg cctgtttagt cccagctact
3961 cgggaggctg aggcaggaga attcttgaa cctgggaggc ggaggtggca gtgagccaag
4021 atcacaccac tacactccag cctgggcaac agagcaagac tccatctcta aataataaat
4081 aaaatggtaa cttttatgta tattttacca aaatttaaaa aattacaagt ttacatttct
4141 taaaatttcc catcaaatct gtaagtaaat ttatgccccg aggaacaagt gctatattta
4201 ttctgagaca acctcctcct tccttaaaca gaatcttagg gctggaggat tgcttcctgc
4261 cctctttgt ttgtgatgta tgcattttga aaattctggg ccgggcgcag tggctcactc
4321 ctgtaatccc agcactttgg gaggccgagg cgggcggatc acaagatcag gagattgaga
4381 ccatcctggc taatacggtg aaaccctgtc tctactgaaa ataacaaaaa attagccggg
4441 cgtggtggcg ggcacctgtg gtcccagcta tttgggaggc tgtggcagga aatggcata
4501 aacctgggag gcggagcttg cagtgagccg agatcgtgcc actgcactcc agcctgggcg
4561 acagagcgag actgcatctc aaaaaaaaaa aaaagaaaa agaaagaaa attctggtat
4621 aatttacata cagtaaaatg cacagatctt agggtttgat gagttttctc tcgacatgtt
4681 tttgcacttc cttgtttttg agaagcactg atttgagaag tcagtggctt tttctcttta
4741 gtttgcaggg tttgctgtga tttgtaatca cgtacttgac ctaggcttcc cttttccacc
4801 atggtagcag aaagggcatg ggatttagag ctttaagtac gcgctctttg cttactgtct
4861 tataccttga gcatgtcact tctcctctca gacttgtttt ctcatctgta aatggatctg
4921 ttgtgaggac tgactgagat aatgttacta aagggcttt gtataatatt taagcagagt
4981 gagaggtaag cttttgtgt aggtcagggg aaatggagaa aataggtgcc ctgactcaga
5041 ccagtctggc tctttttttt ttttttttg gagacggagt cttgctctgt cacccaggct
5101 ggagtgcagt ggcgcgatct cggctcacgg caagctccac ctcctggtt cacaccattc
5161 tcctgcctca gcctcccgag tagctgggac tacaggcgct cgccacacac ctggctaatt
5221 tttttgtatt tttagtagag acgaggtttc accacgttag ccaggacggt cttgatctcc
5281 tgacctcatg atccgcctgc ctcggcctcc caaagtgctg gattacagg tgtgggccac
5341 cgtgccagc caccggtgtg gctctttaac aacctttgct tgtcccgata ggtcaccttt
5401 ggctcttcag agatgcaggg acacgcgatg ggcttctggt taaccaaact gaattatttg
5461 tgccatctct caatgttgac ggacagccta ttttgccaa tatcacactg ccaggtactg
5521 acgttttact ttttaaaaag ataaggttgt tgtggtaagt acaggataga ccacttgaaa
5581 aattaagccc agttctcaat ttttgcctga tgtcaggcac ggtatccaat ctttttgtat
5641 cctattctct accataaata aaatggaagt gatgtatttg tacgttatgt gttaaaggtg
5701 ttatggtgtc tcaaaagcac tttgggctct taagagacaa gcgaaattaa agtatcatat
5761 cataggttag ttttgtagaa ttgtagaatt acgaatgcct tttgtttccc tggccaaatt
5821 gtgccctgga gttccaggag aacaatgtgt agagcatgag atattttggc ttatttgttg
5881 ctgacttcta atttttttta ttttttgag acagaatctc gctgtgttag ctaggctgga
5941 gtgcagtggc gcaatctcgg ctcactgcaa cctccgccta ctgggttcca gcgattctct
```

FIG. 1C

```
6001 tgtctcagcc tcccgagtag ctgggactac aggcgtgtgc cacccactct gataattttt
6061 tgtatttttta gtagagacgg ggtttcaccg tgttagccag gatggtctcc atctcctgac
6121 ctcatgatct gcccgcctac gcctcccaaa gtgctgggat tacaggcatc agccacagca
6181 cctggcctat gtattttcaa tttaacacaa tcaagctcac agtgccaatc agaggtgttt
6241 tttttttttt taatttttat ttttagagag tctcacagtg tcatccaggc tggagtgcag
6301 tggtgcgatt tcagctcact gcaacctctg catcctgggt tcaagtgatt ctcctgcctc
6361 agcctcctgg gtagctgggg ttataggtgc ctgtcaccac acctggctaa ttttttgtatt
6421 tttagtagag atgaggtttc accatgttgg ccaggctgat cttgaactcc tgacctcagg
6481 tgatctgccc acctcagcct cccaaagtgc tgggattaca ggcgtgagcc actgcgtcca
6541 gcctgttttt tttttttttt aaatcattga agattggtat aatacttcac tatttgtttg
6601 aagctcaaat gattttatca gggtaaaccc taataaactg atgttcctgt gggtaaaaaa
6661 aacctcacta aagaccagca gtgtgtggtg gctcctgcct gtaatcatgc ctgtaattcc
6721 agcacttagg gaggctatgg cgggagggtc gcttgagacc aggagttctt gaccagcctg
6781 gacaacaaag tgagacccca gctccacaaa aaaattttttt tttaattacc tgggcatctt
6841 agcatatgcc tgtggtcaca gctatttggg aggcttaggt gggaggatcc cttgagccca
6901 ggagtttgag gctgcagtga gccatgatca taccactgca ctccagccca ggtgacagag
6961 tgagatcctg tctcaaaaaa agaaaaaaaa aactcaaaaa ccccccaaat acatgggttt
7021 cataggatcc aaactactat gtgtgtatag atcctgtttt aaggaagtag atatataaaa
7081 atgagcattg ctaagttaaa tttggtaaat ttgccttata gaacaccctc gagtacgttt
7141 ccagtgagtg taaaatagga attgggatac ccaattcagt tgtactaaat tttctttttt
7201 tttttttttt ttgagacgga gtctcgctct gtcgcccagg ctggagtgca gtggcgggat
7261 ctcggctcac tgcaagctcc gcctcccggg ttcacgccat tctcctgcct cagcctccca
7321 agtagctggg actacaggcg cccgccacta cgcccggcta attttttgta ttttttagtag
7381 agacggggtt tcaccgtttt agccgggatg gtctcgatct cctgacctcg tgatccgccc
7441 gcctcggcct cccaaagtgc tgggattaca ggcgtgagcc accgcgcccg gcctagattt
7501 tctaagtaca cattgttttg gttatgtgtt ttgtgactac caccccaaaa ctaataacca
7561 ccttttttt ttttttgaga cagagtctca ctgtgtcacc caggctggag tgcagtggcg
7621 tgtgatcttg gctcactgca acctctgcct ctcgggttca agtgattctc ctgcttcagc
7681 agctgggact acaggtgtgc accaccaagc ctggctaatt ttttgcattt tagtggagac
7741 gggggtttca ccatgttgac caggctgatc ttaaactctt gagctcaggc agtctgcctg
7801 cctcagcctc ctaaagtgct aggattacag gcgtgagcca ctgcgcccag cccaccgttt
7861 tatttgttca taattctgta gtccaggctg ggctcagcta ggcagttact ctgctggtgg
7921 tagtcgttgg tgtggctgcc ttttgctggc agctggggggc tgggcctgtc cctcttttt
7981 tttttctct ttctttttt ccttttttc aagatagggt ctcactctgt cacccaggtt
8041 ggagtgcagt ggcatgatct tagctcactg caacctctgc tccagggct caagtgatcc
8101 tcccacctca gcctccccag tcgctgggac cacaggcatg tgccaccatg cctggctaat
8161 ttttttgtgta ttttgtagag acggggtttc gccatgttgc caggctggtc tcgaactcct
8221 gagctcaggc gatctactga cgttggcctc ccaaagtgtt gggatcacag gcatgaacca
8281 ccatgcctgg ccaggcctg ttcctcttta tgtggtctct ctagcaggg agctcagggc
8341 tttcaaaagt ataaagcag aagtcagcag gccttttaa ggcttcggcc tagaattgcc
8401 agtgtcgctt catcgacatt cagttagtta aagcaatcac aagcccagcc catttcaagg
8461 tgaaattact acagaggcat gaacaccatg aggtgtccat aggggggccat cagcataaca
8521 cactgccaca tacatgcact cactttttt ctttaaccta aagtgagatc catcagtagt
8581 acaggtagtt gttggcaaag cctcttgttc gttccttgta ctgagaccct agtctgtcac
8641 tgaggatttg gttttttgccc ttccagtgta tactctgaaa gagcgatgcc tccaggttgt
8701 ccggagccta gtcaagcctg agaattacag gagactggac atcgtcaggt cgctctacga
8761 agatctggaa gaccacccaa atgtgcagaa agacctggag cggctgacac aggagcgcat
8821 tgcacatcaa cggatgggag attgaagatt tctgttgaaa cttacactgt ttcatctcag
8881 cttttgatgg tactgatgag tcttgatcta gatacaggac tggttccttc cttagtttca
8941 aagtgtctca ttctcagagt aaaataggca ccattgctta aagaaagtt aactgacttc
9001 actaggcatt gtgatgttta ggggcaaaca tcacaaaatg taatttaatg cctgcccatt
9061 agagaagtat ttatcaggag aaggtggtgg cattttttgct tcctagtaag tcaggacagc
9121 ttgtatgtaa ggaggtttat ataagtaatt cagtgggaat tgcagcatat cgtttaattt
9181 taagaaggca ttggcatctg cttttaatgg atgtataata catccattct acatccgtag
9241 cggttggtga cttgtctgcc tcctgctttg ggaagactga ggcatccgtg aggcagggac
9301 aagtctttct cctctttgag accccagtgc ctgcacatca tgagccttca gtcagggttt
9361 gtcagaggaa caaaccaggg gacactttgt tagaaagtgc ttagaggttc tgcctctatt
9421 tttgttgggg ggtgggagag gggaccttaa aatgtgtaca gtaacaaat gtcttaaagg
9481 gaatcatttt tgtaggaagc atttttttata atttttctaag tcgtgcactt tctcggtcca
9541 ctcttgttga agtgctgttt tattactgtt tctaaactag gattgacatt ctacagttgt
```

```
 9601 gataatagca ttttttgtaac ttgccatccg cacagaaaat acgagaaaat ctgcatgttt
 9661 gattatagta ttaatggaca aataagtttt tgctaaatgt gagtatttct gttccttttt
 9721 gtaaatatgt gacattcctg attgatttgg gttttttttgt tgttgttgtt ttgttttgtt
 9781 ttgttttttt gggatggagk ctcactcttg tcacccaggc tggagtgcag tggcgccatc
 9841 tcggctcact gcaacctctg cctcctgagt tcacgtaatc ctcctgagta gctgggatta
 9901 caggtgcctg ccaccacgct ggccaatttt tgtactttta gtagagacag tgtttcgcca
 9961 tgttggccag gctggtttca aactcctgac ctcaggtgat ccgcccacct cagcctccca
10021 aaatggtggg attacaggtg tgtgggccac cgtgcctggc tgattcagca ttttttatca
10081 ggcaggacca ggtggacttc cacctccagc ctctggtcct accaatggat tcatggagta
10141 gcctggactg tttcatagtt ttctaaatgt acaaattctt ataggctaga cttagattca
10201 ttaactcaaa ttcaatgctt ctatcagact cagttttttg taactaatag atttttttt
10261 ccacttttgt tctactcctt ccctaatagc ttttaaaaa aatctcccca gtagagaaac
10321 atttggaaaa gacagaaaac taaaaaggaa gaaaaaagat ccctattaga tacacttctt
10381 aaatacaatc acattaacat tttgagctat ttccttccag cctttttagg gcagattttg
10441 gttggttttt acatagttga gattgtactg ttcatacagt tttatatccct ttttcattta
10501 actttataac ttaaatattg ctctatgtta gtataagctt ttcacaaaca ttagtatagt
10561 ctcccttta taattaatgt ttgtgggtat ttcttggcat gcatctttaa ttccttatcc
10621 tagcctttgg gcacaattcc tgtgctcaaa aatgagagtg acggctggca tggtggctcc
10681 cgcctgtaat cccagtactt tgggaagcca aggtcaagagg attgcttgag cccagaactt
10741 caagatgagc ctgggctcat agtgagaacc cgtctataca aaaaattttt aaaaattagc
10801 atggcggcac acatctgtaa tcctagctac ttggcaggct gaggtgagaa gatcattgga
10861 gtttaggaat tggaggcggc agtgagtcat gagtgatgccg ctgcactcca gcctggggga
10921 cagagcaaga ccctgcctca aaaaaaaaaa aaaaaaaaat tcaggccggg aatggtggtt
10981 cacgcctgta atcccagcac tttgggggggt cgaggtgggc agatcacctg aggtcaggag
11041 ttcgagacca gcctggccaa catggtaaaa ccccattct actaaaaaat acaagaatta
11101 gctgggtgtg gtggcgcatg cctgtaatcc tagctactca ggaggctgag gcaggagaat
11161 cacttgaccc caggaggcga agattgcagt gagctgatat cgcaccattg tactccagcc
11221 tgtgtgacag agcaatactc ttgtcccaaa aaaaaaaaaa attcaaatca gagtgaagtg
11281 aatgagacac tccagttttc cttctactcc gaattttagc tcctccttt aacattcaac
11341 aaatagtctt ttttttttt ttttttttt gggatggag tctccctctg ttgcccaggc
11401 tggagtgcag aggtgcgatc tctgctcact acaagctctg cctcccgagt tcaagtgatt
11461 ctcctggctc accctcctga gctgggatta caggcgcctg ccaccatgcc tggctaattt
11521 tgtgttttta gtggagacgg ggtttcacca tgttgtccag gatggtcttg atctcctgac
11581 cttgtgatcc acccacctca gcctcccaaa gtggtgggat tacaggtgtg agccaccgcg
11641 tccagccagc tttattattt tttttaagct gtctttgtgt caaaatgata gttcatgctc
11701 ctcttgttaa aacctgcagg ccgagcacag tggctcatgc ctgtaatccc agcatttttgg
11761 gagaccaagg cggatggatc acctgaggtc aggagctcaa gaccagcctg gctaacatgg
11821 tgaaaccctca tctccactta aaatacaaaa attgccggcc gcggcggctc atgcctgtaa
11881 tcccagcact tgggaggcc taggcgggtg gatcacgacg tcaggaaatc gagaccatcc
11941 tggctaacac gggtgaaacc ccgtctctat taaaaaatag aaaaaattag gcgggcgtgg
12001 tggtgagcgc ctgtagtccc agctactcga gagcctgagg caggagaatg gcatgaacct
12061 ggaaggtgga gcttgcagtg agctgagatg gtgccactgc actctaacct gggcgacaga
12121 gtgagactcc gtctcaaaaa aaaaaacaaa aaccaaaact tatccaggtg tggcggtggg
12181 cgcctgtgag gcaggcgaat ctcttgaacc cgggaggcgg aggttgcagt gagccaagat
12241 cacaccattg cactccagcc tgggaaacaa gagtgaaatt ccatctcaaa accaaatttt
12301 caaaaaaaaa acatgccgct tgagtactgt gttttggtg ttgtccaagg aaaattaaaa
12361 cctgtagcat gaataatgtt tgttttcatt tcgaatcttg tgaatgtatt aaatatatcg
12421 ctcttaagag acggtgaagt tcctatttca agtttttttt gttttgtttt gttttttaagc
12481 tgtttttttaa tacattaaat ggtgctgagt aaggaaata ggcagggtgt gttgtgtggt
12541 gttttaacta ggcgcttctc tctcagagag ttttgaaacc tgtttacata aaggcccaag
12601 atgggaagga gatccaaaca taagccacca gcctcattcc aagtctcttc tcttttccaac
12661 cctggatttt tttttttat ttaacattgt ttctttagc tttatttttc ttataaaga
12721 aatgtatcac tataaaaaat tacacactac agaaaaatat taagaagaaa aacattcaca
12781 tcggaaacaa agtttttttcc catgaaaaca gaacccaaaa gggtaagtgg ttagtatttc
12841 accagcaatt atgttgagaa taaggccagg cgaggtggct cacgcctgta atctcagcac
12901 tttgggaggc cagggcaggc agatcatctg aggtcaggag tttgagacca gcctggccaa
12961 catggtgaaa ccctatctct actaaaaatt aaaaaattag ctgggtgtgg tggcatgtac
13021 ctgtaatccc agctattcag gaggctgagg caggagaatt gcttgaacct gggaggcgga
13081 ggttgcagtg agctgagatt gcaccattgc actctagcct gggcaacgag tgaaactccg
13141 tctcaaaaga aaaaaatata tatatataga gagagagaga gagagaatac cacagtgagg
```

FIG. 1E

```
13201 gcatgggcta gaaatcagtg cactaaggat atgaaataga tgtcaatgtg aactttttcgg
13261 atactttgac cctgggtctt tgtatcctct tcttagcacc tcagtcccac gctctgctag
13321 tcattggctt cctgataccc cttcaataca gactgagtat ccctaatcca aaaatttcaa
13381 atccaaagca ctccaaaatc caagagtcca acgtgacgcc acaagtggaa agttccacat
13441 gcgagtactt aacacaaact tgtttcacgt gcaaaaactgg ggaaaatatt gcttacaatt
13501 acctacagcc tgtgtctata agtgtttat gaaactggtg ttatgatgta tatgttttct
13561 ttttttgttc ctggctcata actccatag cccttgttac ggatgtgagc caccttgcct
13621 ggctgatttt taagtttttt gtagagatgg ggtctcgctg tgttgccctg gctggtttta
13681 actcctgggc tcaagcgatc ctcccacctt ggcctcccaa agccctggga ttacaggtga
13741 gattacaacc ctcatttcag agaaggtcct acccatacc ctgggggaag gaatggtgac
13801 atcataaagc ctcgttaaaa cccatgagag cagtggagag tgtcaggata gctgaactac
13861 gtgtagaggt tcctggaggg tggtgcgccc agggaggga cagaagctct gcgcccctta
13921 tcccatacct tggtgtacgc atctcttcat ctgtatcctt cgtaatatcc tttatgataa
13981 accaggtagg ccgggcgtgg tggctcacac atataatccc agcactttgg gaggctgagg
14041 taggaggatt gcttcagcct gggagttcaa gataacatca tagtgagatc ctgtctctac
14101 tagaaaaaaa aagaacaaac aggagtggtg gcgcatgctt gcagtcccag ctgttcagtt
14161 tgcactccag cctgggagac agagcaagac ctgctgtctc aaaaaaaaaa gactgtaaa
14221 cattttcac tgagttctgt tagccactcc agcaaattaa acccaaagcg aaggtggtgg
14281 gaaccccaac ttgaagctgg ttggtcagaa gttctggagc cctaaacttg ctactggtgt
14341 gtgggtgggg gcagtcttgg ggactgaggc ctcaacctgc aggatctgat attatttcca
14401 gaaagatggt gttgaagtg aattagagga taccctaattg gtgttcactg cagaattgat
14461 tgcttgctcg ctctcgggaa gaaatctaca catttggaca cgaaagtgtt ctgggttggt
14521 attgtgttag tgtggaatct aga (SEQ ID NO: 17)
```

FIG. 1F

MEGAGGANDKKKISSERRKEKSRDAARSRRSKESEVFYELAHQL
PLPHNVSSHLDKASVMRLTISYLRVRKLLDAGDLDIEDDMKAQMNCFYLKALDGFVMV
LTDDGDMIYISDNVNKYMGLTQFELTGHSVFDFTHPCDHEEMREMLTHRNGLVKKGKE
QNTQRSFFLRMKCTLTSRGRTMNIKSATWKVLHCTGHIHVYDTNSNQPQCGYKKPPMT
CLVLICEPIPHPSNIEIPLDSKTFLSRHSLDMKFSYCDERITELMGYEPEELLGRSIY
EYYHALDSDHLTKTHHDMFTKGQVTTGQYRMLAKRGGYVWVETQATVIYNTKNSQPQC
IVCVNYVVSGIIQHDLIFSLQQTECVLKPVESSDMKMTQLFTKVESEDTSSLFDKLKK
EPDALTLLAPAAGDTIISLDFGSNDTETDDQQLEEVPLYNDVMLPSPNEKLQNINLAM
SPLPTAETPKPLRSSADPALNQEVALKLEPNPESLELSFTMPQIQDQTPSPSDGSTRQ
SSPEPNSPSEYCFYVDSDMVNEFKLELVEKLFAEDTEAKNPFSTQDTDLDLEMLAPYI
PMDDDFQLRSFDQLSPLESSSASPESASPQSTVTVFQQTQIQEPTANATTTTATTDEL
KTVTKDRMEDIKILIASPSPTHIHKETTSATSSPYRDTQSRTASPNRAGKGVIEQTEK
SHPRSPNVLSVALSQRTTVPEEELNPKILALQNAQRKRKMEHDGSLFQAVGIGTLLQQ
PDDHAATTSLSWKRVKGCKSSEQNGMEQKTIILIPSDLACRLLGQSMDESGLPQLTSY
DCEVNAPIQGSRNLLQGEELLRALDQVN (SEQ ID NO: 18)

FIG. 2A

```
   1 gtgaagacat cgcggggacc gattcaccat ggagggcgcc ggcggcgcga acgacaagaa
  61 aaagataagt tctgaacgtc gaaaagaaaa gtctcgagat gcagccagat ctcggcgaag
 121 taaagaatct gaagtttttt atgagcttgc tcatcagttg ccacttccac ataatgtgag
 181 ttcgcatctt gataaggcct ctgtgatgag gcttaccatc agctatttgc gtgtgaggaa
 241 acttctggat gctggtgatt tggatattga agatgacatg aaagcacaga tgaattgctt
 301 ttatttgaaa gccttggatg gttttgttat ggttctcaca gatgatggtg acatgattta
 361 catttctgat aatgtgaaca aatacatggg attaactcag tttgaactaa ctggacacag
 421 tgtgtttgat tttactcatc catgtgacca tgaggaaatg agagaaatgc ttacacacag
 481 aaatggcctt gtgaaaaagg gtaaagaaca aaacacacag cgaagctttt ttctcagaat
 541 gaagtgtacc ctaactagcc gaggaagaac tatgaacata aagtctgcaa catggaaggt
 601 attgcactgc acaggccaca ttcacgtata tgataccaac agtaaccaac ctcagtgtgg
 661 gtataagaaa ccacctatga cctgcttggt gctgatttgt gaacccattc ctcacccatc
 721 aaatattgaa attcctttag atagcaagac tttcctcagt cgacacagcc tggatatgaa
 781 attttcttat tgtgatgaaa gaattaccga attgatggga tatgagccag aagaactttt
 841 aggccgctca atttatgaat attatcatgc tttggactct gatcatctga ccaaaactca
 901 tcatgatatg tttactaaag gacaagtcac cacaggacag tacaggatgc ttgccaaaag
 961 aggtggatat gtctgggttg aaactcaagc aactgtcata tataacacca agaattctca
1021 accacagtgc attgtatgtg tgaattacgt tgtgagtggt attattcagc acgacttgat
1081 tttctccctt caacaaacag aatgtgtcct taaaccggtt gaatcttcag atatgaaaat
1141 gactcagcta ttcaccaaag ttgaatcaga agatacaagt agcctctttg acaaacttaa
1201 gaaggaacct gatgctttaa ctttgctggc cccagccgct ggagacacaa tcatatcttt
1261 agattttggc agcaacgaca cagaaactga tgaccagcaa cttgaggaag taccattata
1321 taatgatgta atgctcccct cacccaacga aaaattacag aatataaatt tggcaatgtc
1381 tccattaccc accgctgaaa cgccaaagcc acttcgaagt agtgctgacc ctgcactcaa
1441 tcaagaagtt gcattaaaat tagaaccaaa tccagagtca ctggaacttt cttttaccat
1501 gccccagatt caggatcaga cacctagtcc ttccgatgga agcactagac aaagttcacc
1561 tgagcctaat agtcccagtg aatattgttt ttatgtggat agtgatatgg tcaatgaatt
1621 caagttggaa ttggtagaaa aacttttttgc tgaagacaca gaagcaaaga acccatttc
1681 tactcaggac acagatttag acttggagat gttagctccc tatatcccaa tggatgatga
1741 cttccagtta cgttccttcg atcagttgtc accattagaa agcagttccg caagccctga
1801 aagcgcaagt cctcaaagca cagttacagt attccagcag actcaaatac aagaacctac
1861 tgctaatgcc accactacca ctgccaccac tgatgaatta aaaacagtga caaaagaccg
1921 tatggaagac attaaaatat tgattgcatc tccatctcct acccacatac ataaagaaac
1981 tactagtgcc acatcatcac catatagaga tactcaaagt cggacagcct caccaaacag
2041 agcaggaaaa ggagtcatag aacagacaga aaaatctcat ccaagaagcc ctaacgtgtt
2101 atctgtcgct ttgagtcaaa gaactacagt tcctgaggaa gaactaaatc caaagatact
2161 agctttgcag aatgctcaga gaaagcgaaa aatggaacat gatggttcac ttttttcaagc
2221 agtaggaatt ggaacattat tacagcagcc agacgatcat gcagctacta catcactttc
2281 ttggaaacgt gtaaaaggat gcaaatctag tgaacagaat ggaatggagc aaaagacaat
2341 tattttaata ccctctgatt tagcatgtag actgctgggg caatcaatgg atgaaagtgg
2401 attaccacag ctgaccagtt atgattgtga agttaatgct cctatacaag gcagcagaaa
2461 cctactgcag ggtgaagaat tactcagagc tttggatcaa gttaactgag cttttcttta
2521 atttcattcc tttttttgga cactggtggc tcactaccta aagcagtcta tttatatttt
2581 ctacatctaa ttttagaagc ctggctacaa tactgcacaa acttggttag ttcaattttt
2641 gatcccttt ctacttaatt tacattaatg ctcttttta gtatgttctt taatgctgga
2701 tcacagacag ctcatttctc cagttttttg gtatttaaac cattgcattg cagtagcatc
2761 attttaaaaa atgcaccttt ttatttattt attttggct agggagttta tcccttttc
```

FIG. 2B

```
2821  gaattatttt  taagaagatg  ccaatataat  ttttgtaaga  aggcagtaac  ctttcatcat
2881  gatcataggc  agttgaaaaa  ttttacacc  ttttttttca  cattttacat  aaataataat
2941  gcttgccag  cagtacgtgg  tagccacaat  tgcacaatat  attttcttaa  aaaataccag
3001  cagttactca  tggaatatat  tctgcgttta  taaaactagt  ttttaagaag  aaattttttt
3061  tggcctatga  aattgttaaa  cctggaacat  gacattgtta  atcatataat  aatgattctt
3121  aaatgctgta  tggtttatta  tttaaatggg  taaagccatt  tacataatat  agaaagatat
3181  gcatatatct  agaaggtatg  tggcatttat  ttggataaaa  ttctcaattc  agagaaatca
3241  tctgatgttt  ctatagtcac  tttgccagct  caaagaaaaa  caatacccta  tgtagttgtg
3301  gaagtttatg  ctaatattgt  gtaactgata  ttaaacctaa  atgttctgcc  taccctgttg
3361  gtataaagat  atttgagca  gactgtaaac  aagaaaaaaa  aaatcatgca  ttccttagcaa
3421  aattgcctag  tatgttaatt  tgctcaaaat  acaatgtttg  attttatgca  ctttgtcgct
3481  attaacatcc  ttttttttcat  gtagatttca  ataattgagt  aattttagaa  gcattatttt
3541  aggaatatat  agttgtcaca  gtaaatatct  tgttttttct  atgtacattg  tacaaatttt
3601  tcattccttt  tgctcttgt  ggttggatct  aacactaact  gtattgtttt  tacaaatttt
3661  ataaacatct  tctgtgga  (SEQ ID NO: 19)
```

FIG. 2C

SEQUENCE LISTING

<160> NUMBER OF SEQ ID NOS: 19

<210> SEQ ID NO 1
<211> LENGTH: 8
<212> TYPE: PRT
<213> ORGANISM: Homo sapiens

<400> SEQUENCE: 1

Leu Ala Pro Tyr Ile Pro Met Asp
 1               5

<210> SEQ ID NO 2
<211> LENGTH: 8
<212> TYPE: PRT
<213> ORGANISM: Homo sapiens

<400> SEQUENCE: 2

Leu Ala Pro Tyr Ile Ser Met Asp
 1               5

<210> SEQ ID NO 3
<211> LENGTH: 8
<212> TYPE: PRT
<213> ORGANISM: Artificial Sequence
<220> FEATURE:
<223> OTHER INFORMATION: Motif

<400> SEQUENCE: 3

Leu Leu Pro Tyr Ile Pro Met Asp

-continued

```
<210> SEQ ID NO 4
<211> LENGTH: 8
<212> TYPE: PRT
<213> ORGANISM: Artificial Sequence
<220> FEATURE:
<223> OTHER INFORMATION: Motif

<400> SEQUENCE: 4

Leu Val Pro Tyr Ile Pro Met Asp
 1               5

<210> SEQ ID NO 5
<211> LENGTH: 8
<212> TYPE: PRT
<213> ORGANISM: Artificial Sequence
<220> FEATURE:
<223> OTHER INFORMATION: Motif

<400> SEQUENCE: 5

Ile Ala Pro Tyr Ile Pro Met Asp
 1               5

<210> SEQ ID NO 6
<211> LENGTH: 8
<212> TYPE: PRT
<213> ORGANISM: Artificial Sequence
<220> FEATURE:
<223> OTHER INFORMATION: Motif

<400> SEQUENCE: 6

Ile Ala Pro Tyr Ile Pro Met Glu
 1               5

<210> SEQ ID NO 7
<211> LENGTH: 8
<212> TYPE: PRT
<213> ORGANISM: Artificial Sequence
<220> FEATURE:
<223> OTHER INFORMATION: Motif

<400> SEQUENCE: 7

Leu Val Pro Tyr Ile Ser Met Asp
 1               5

<210> SEQ ID NO 8
<211> LENGTH: 19
<212> TYPE: PRT
<213> ORGANISM: Artificial Sequence
<220> FEATURE:
<223> OTHER INFORMATION: Motif

<400> SEQUENCE: 8

Asp Leu Asp Leu Glu Met Leu Ala Pro Tyr Ile Pro Met Asp Asp
 1               5                  10                  15

Phe Gln Leu

<210> SEQ ID NO 9
<211> LENGTH: 34
<212> TYPE: PRT
<213> ORGANISM: Artificial Sequence
<220> FEATURE:
<223> OTHER INFORMATION: Synthetic peptide

<400> SEQUENCE: 9
```

```
Pro Phe Ser Thr Gln Asp Thr Asp Leu Asp Leu Glu Met Leu Ala Pro
 1               5                  10                  15

Tyr Ile Pro Met Asp Asp Asp Phe Gln Leu Arg Ser Phe Asp Gln Leu
            20                  25                  30

Ser Pro
```

<210> SEQ ID NO 10
<211> LENGTH: 16
<212> TYPE: PRT
<213> ORGANISM: Drosophila melanogaster

<400> SEQUENCE: 10

```
Arg Gln Ile Lys Ile Trp Phe Gln Asn Arg Arg Met Lys Trp Lys Lys
 1               5                  10                  15
```

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
agggacacac gatgggcttc tg                                          22

<210> SEQ ID NO 12
<211> LENGTH: 74
<212> TYPE: DNA
<213> ORGANISM: Artificial Sequence
<220> FEATURE:
<223> OTHER INFORMATION: Primer

<400> SEQUENCE: 12
gcagaattcg gcttcacaag ctagcgtaat ctggaacatc gtatgggtat ccatctccca    60
tccgttgatg tggc                                                     74

<210> SEQ ID NO 13
<211> LENGTH: 24
<212> TYPE: DNA
<213> ORGANISM: Mus sp.

<400> SEQUENCE: 13
cgcgtcgtgc aggacgtgac aaat                                          24

<210> SEQ ID NO 14
<211> LENGTH: 24
<212> TYPE: DNA
<213> ORGANISM: Mus sp.

<400> SEQUENCE: 14
gccctacgtg ctgcctcgca tggc                                          24

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide probe

<400> SEQUENCE: 15
gccctacgtg ctgcctcgca tggc                                          24

<210> SEQ ID NO 16

<211> LENGTH: 213
<212> TYPE: PRT
<213> ORGANISM: Homo sapiens

<400> SEQUENCE: 16

```
Met Pro Arg Arg Ala Glu Asn Trp Asp Glu Ala Glu Val Gly Ala Glu
 1               5                  10                  15
Glu Ala Gly Val Glu Glu Tyr Gly Pro Glu Glu Asp Gly Gly Glu Glu
            20                  25                  30
Ser Gly Ala Glu Glu Ser Gly Pro Glu Glu Ser Gly Pro Glu Glu Leu
        35                  40                  45
Gly Ala Glu Glu Glu Met Glu Ala Gly Arg Pro Arg Pro Val Leu Arg
    50                  55                  60
Ser Val Asn Ser Arg Glu Pro Ser Gln Val Ile Phe Cys Asn Arg Ser
65                  70                  75                  80
Pro Arg Val Val Leu Pro Val Trp Leu Asn Phe Asp Gly Glu Pro Gln
                85                  90                  95
Pro Tyr Pro Thr Leu Pro Pro Gly Thr Gly Arg Arg Ile His Ser Tyr
            100                 105                 110
Arg Gly His Leu Trp Leu Phe Arg Asp Ala Gly Thr His Asp Gly Leu
        115                 120                 125
Leu Val Asn Gln Thr Glu Leu Phe Val Pro Ser Leu Asn Val Asp Gly
    130                 135                 140
Gln Pro Ile Phe Ala Asn Ile Thr Leu Pro Val Tyr Thr Leu Lys Glu
145                 150                 155                 160
Arg Cys Leu Gln Val Val Arg Ser Leu Val Lys Pro Glu Asn Tyr Arg
                165                 170                 175
Arg Leu Asp Ile Val Arg Ser Leu Tyr Glu Asp Leu Glu Asp His Pro
            180                 185                 190
Asn Val Gln Lys Asp Leu Glu Arg Leu Thr Gln Glu Arg Ile Ala His
        195                 200                 205
Gln Arg Met Gly Asp
        210
```

<210> SEQ ID NO 17
<211> LENGTH: 14543
<212> TYPE: DNA
<213> ORGANISM: Homo sapiens

<400> SEQUENCE: 17

| | | | | |
|---|---|---|---|---|
| gaattcagtt | agttgacttt | ttgtactttta | taagcgtgat | gattgggtgt tcccgtgtga | 60 |
| gatgcgccac | cctcgaacct | tgttacgacg | tcggcacatt | gcgcgtctga catgaagaaa | 120 |
| aaaaaaattc | agttagtcca | ccaggcacag | tggctaaggc | ctgtaatccc tgcactttga | 180 |
| gaggccaagg | caggaggatc | acttgaaccc | aggagttcga | gaccagccta ggcaacatag | 240 |
| cgagactccg | tttcaaacaa | caaataaaaa | taattagtcg | ggcatggtgg tgcgcgccta | 300 |
| cagtaccaac | tactcgggag | gctgaggcga | gacgatcgct | tgagccaggg aggtcaaggc | 360 |
| tgcagtgagc | caagctcgcg | ccactgcact | ccagcccggg | cgacagagtg agaccctgtc | 420 |
| tccaaaaaaa | aaaaaaaaca | ccaaaccttta | gagggtgaa | aaaaaatttt atagtggaaa | 480 |
| tacagtaacg | agttggccta | gcctcgcctc | cgttacaaca | gcctacggtg ctggaggatc | 540 |
| cttctgcgca | cgcgcacagc | ctccggccgg | ctatttccgc | gagcgcgttc atcctctac | 600 |
| cgagcgcgcg | cgaagactac | ggaggtcgac | tcgggagcgc | gcacgcagct ccgcccccgcg | 660 |
| tccgacccgc | ggatcccgcg | gcgtccggcc | cgggtggtct | ggatcgcgga gggaatgccc | 720 |

-continued

```
cggagggcgg agaactggga cgaggccgag gtaggcgcgg aggaggcagg cgtcgaagag      780
tacggccctg aagaagacgg cggggaggag tcgggcgccg aggagtccgg cccggaagag      840
tccgccccgg aggaactggg cgccgaggag gagatggagg ccgggcggcc gcggcccgtg      900
ctgcgctcgg tgaactcgcg cgagccctcc caggtcatct tctgcaatcg cagtccgcgc      960
gtcgtgctgc ccgtatggct caacttcgac ggcgagccgc agccctaccc aacgctgccg     1020
cctggcacgg gccgccgcat ccacagctac cgaggtacgg gcccggcgct taggcccgac     1080
ccagcaggga cgatagcacg gtctgaagcc cctctaccgc cccggggtcc attttgcaga     1140
cggggaactg aggccccttg aggcaggaca catccagggt gacgctgctc gtaagcgtca     1200
gagcattctt tttttttttt tttttttttt tctgagacgg agtctcgctc tgtcgcccag     1260
gctggagtgc agtggcgcga tctcgactca ctgcagcctc cgcctccggg gttcaagcga     1320
ttctcctgcc tcagcctcct gagtagctgg gattacaggc gtgcgccacc gcgcccggct     1380
gattttata tttttagtag acgggggtt tcaccatgtt ggtcaggctg gtctcgaact      1440
aactgacctc gtgatccgcc cgcctcggcc ttcccaaagt gctgggctta tgggcatgag     1500
cctccgcgcc cggcccagag cattctttat aaggccgaat agtttgcatt tgaaggtggc     1560
tcccccccag tccccaccc cacgtgtatt ttcccctcaa agaaaagctg catccttaac      1620
accccatctg ttcagtcctc atgactccag tgggccagtt ctgcgtagtc cctgccctcg     1680
tggagaacac attcctcctg gggagactga cagatgcaaa gacaggaaca agccagggtc     1740
atgttggcgc cggaagagcc gaccgtgtgt ggcgtgggaa attgacttac ctgcctgctg     1800
ggagatggag gggttgcggt tgtgtggttt cagttaagga gcacttcccg gagaaggaag     1860
agagcaggat ggagtaggaa ctagccaacc ctaggtaaga ggttctagac atgcgtgcgt     1920
tgagacctgg agtcttggga gaggatgctt aaaaggtgat tttacccta ggaatatggg      1980
ggcactgaaa ttttttttt tttttgagac gggagtcttg ctctgcaagc tggagtgcag     2040
tggcccacgc tagaatgcag tggcgcgatt gcggctcatt gcaacatctg ccacctgggg     2100
tcaagtggtt ctcttgcctc agcctcccga ggagcgggga ttactggcgt gcgccaccac     2160
tcctggctaa tttttttttt agtagagacg ggggtttcgt cattttggct aggctggtct     2220
cgaactcctg acctcagatg atccacccgc cttggcctcc caaagtgctg agattacagg     2280
tgtaagccac tgcgcccagc cctttgaaag tttttcagta tttatgtata tatatttttg     2340
agttggagtc tggatctgtc gccagactgg agtgctgttg cacaatcttg gctcactgca     2400
atctccgact ccctggttca agcgattctc ctgcctcagc ctcccaagta gctgggatta     2460
caggcacgca ctaccattcc cagctaattt tttgtattct tagtagagac agggtttcac     2520
catgttggcc aggatggtct ccatctcctg cgctcgtgat ctgcctgctt cggcctccca     2580
aagtgctggg attacaggcg tgctgggatt tcggccacaa cgtccgaccg aaagttttta     2640
agcagggaca tgacattgtc agatttatat actgaaaagc tcacccaggt tgccaagtgg     2700
tttgaggggg aaagactgct gtcgaggaag cagttaggta gttgtgaaaa cccaggtgag     2760
gaataactag gccttaccta aggtgcaggc agtaatcttg ccatggcctt taagcagaga     2820
agtagtccta gtgtcactta atcttttacaa aggattttg caaggatccc gatctttctt      2880
ccttgagggt ggtgtactta atacacttt acaccagact tctaatgtta gatgaagaac      2940
acagtatttc cagggatcaa catttctgta ggctcctatt ttatatagga aattgtatga     3000
attttgtatt ttactccaaa attttctgt gcccgattta atataaaaat ttactgagcc      3060
```

```
tgggtgcagt ggctcatgcc tgtgatctca gcactttggg aggctgaggc aggaggattt      3120
cttgagccca ggagctggag accagcctgt gcaacatagt gagaccctgt ctgtatttaa      3180
aaaaaaaaaa aaattcttga aaaattagca gggcacattc ctgcctttag tcccagctac      3240
ttgggaagct gaggcaggaa gatcacccga acccaggagt tggaggctac agtgaactat      3300
gatggtgcct ctgaatagtt gctgtactct agtctggtaa cacagcaaga ccctgtctct      3360
ctatcttgtc tttttttttt ttttttttttg agacaggatg tcctgctgtt gcctgggctg      3420
gagtgtggag ctggagtttt ggtggcatga tcacggctca ttgcacccct aacctgggct      3480
caagcagtcc tcccagagct tcagcttccc aaagtagctg ggactatagg catgctccac      3540
tatgtctggc taatttcttt ttttattttt attttttagta gagatgaggt cttgctatgt      3600
tgcccaggct gagacctcat ctcttttta tttttttaa attttttatt atactttaag         3660
ttctagggta catgtgcaca acgtgcaggt ttgttacata tgtaaacatg tgccatgttg      3720
gtgtgctgca cccatagaga cctcgtctta aaaaagaaa ataacattac ttttgaaggt        3780
acttaatgca ctgaattgta catttaaaaa tggttaaaat ggtaaatgtt tgaggcaggt      3840
agatccacct gaggtcagga gttcaagacc agcctgacca atatggtgga accctgtctc      3900
tgctaaaaat acaaaagtta gctgcatgtg gtggcatgcg cctgtttagt cccagctact      3960
cgggaggctg aggcaggaga attgcttgaa cctgggaggc ggaggtggca gtgagccaag      4020
atcacaccac tacactccag cctgggcaac agagcaagac tccatctcta ataataaat      4080 aaaatggtaa cttttatgta tattttacca aaatttaaaa aattacaagt ttacatttct      4140
taaaatttcc catcaaatct gtaagtaaat ttatgccccg aggaacaagt gctatattta      4200
ttctgagaca acctcctcct tccttaaaca gaatcttagg gctggaggat tgcttcctgc      4260
cctcttttgt ttgtgatgta tgcattttga aaattctggg ccgggcgcag tggctcactc      4320
ctgtaatccc agcactttgg gaggccgagg cgggcggatc acaagatcag gagattgaga      4380
ccatcctggc taatacggtg aaaccctgtc tctactgaaa ataacaaaaa attagccggg      4440
cgtggtggcg gcacctgtg gtcccagcta tttgggaggc tgtggcagga gaatggcata      4500
aacctgggag gcggagcttg cagtgagccg agatcgtgcc actgcactcc agcctgggcg      4560
acagagcgag actgcatctc aaaaaaaaaa aaaagaaaa agaaaagaaa attctggtat      4620
aatttacata cagtaaaatg cacagatctt agggtttgat gagttttctc tcgacatgtt      4680
tttgcacttc cttgtttttg agaagcactg atttgagaag tcagtggctt tttctcttta      4740
gtttgcaggg tttgctgtga tttgtaatca cgtacttgac ctaggcttcc cttttccacc      4800
atggtagcag aaaggcatg ggatttagag ctttaagtac gcgctctttg cttactgtct        4860
tataccttga gcatgtcact tctcctctca gacttgtttt ctcatctgta aatggatctg      4920
ttgtgaggac tgactgagat aatgttacta gaagggcttt gtataatatt taagcagagt      4980
gagaggtaag ctttttgtgt aggtcagggg aaatggagaa aataggtgcc ctgactcaga      5040
ccagtctggc tcttttttttt ttttttttg agacggagt cttgctctgt cacccaggct       5100
ggagtgcagt ggcgcgatct cggctcacgg caagctccac ctcctgggtt cacaccattc      5160
tcctgcctca gcctcccgag tagctgggac tacaggcgct cgccacacac ctggctaatt      5220 ttttttgtatt tttagtagag acgaggtttc accacgttag ccaggacggt cttgatctcc      5280
tgacctcatg atccgcctgc ctcggcctcc caaagtgctg ggattacagg tgtgggccac      5340
cgtgcccagc caccggtgtg gctctttaac aacctttgct tgtcccgata ggtcaccttt      5400
ggctcttcag agatgcaggg acacacgatg ggcttctggt taaccaaact gaattatttg      5460
```

```
tgccatctct caatgttgac ggacagccta ttttgccaa tatcacactg ccaggtactg    5520
acgttttact ttttaaaaag ataaggttgt tgtggtaagt acaggataga ccacttgaaa    5580
aattaagccc agttctcaat ttttgcctga tgtcaggcac ggtatccaat cttttgtat    5640
cctattctct accataaata aaatggaagt gatgtatttg tacgttatgt gttaaaggtg    5700
ttatggtgtc tcaaaagcac tttgggctct taagagacaa gcgaaattaa agtatcatat    5760
cataggttag ttttgtagaa ttgtagaatt acgaatgcct tttgtttccc tggccaaatt    5820
gtgccctgga gttccaggag aacaatgtgt agagcatgag atattttggc ttatttgttg    5880
ctgacttcta atttttttta ttttttgag acagaatctc gctgtgttag ctaggctgga    5940
gtgcagtggc gcaatctcgg ctcactgcaa cctccgccta ctgggttcca gcgattctct    6000
tgtctcagcc tcccgagtag ctgggactac aggcgtgtgc cacccactct gataattttt    6060
tgtatttta gtagacacgg ggtttcaccg tgttagccag gatggtctcc atctcctgac    6120
ctcatgatct gcccgcctac gcctcccaaa gtgctgggat tacaggcatc agccacagca    6180
cctggcctat gtattttcaa tttaacacaa tcaagctcac agtgccaatc agaggtgttt    6240
tttttttttt taatttttat ttttagagag tctcacagtg tcatccaggc tggagtgcag    6300
tggtgcgatt tcagctcact gcaacctctg catcctgggt tcaagtgatt ctcctgcctc    6360
agcctcctgg gtagctgggg ttataggtgc ctgtcaccac acctggctaa tttttgtatt    6420
tttagtagag atgaggtttc accatgttgg ccaggctgat cttgaactcc tgacctcagg    6480
tgatctgccc acctcagcct cccaaagtgc tgggattaca ggcgtgagcc actgcgtcca    6540
gcctgttttt tttttttttt aaatcattga agattggtat aatacttcac tatttgtttg    6600
aagctcaaat gattttatca gggtaaaccc taataaactg atgttcctgt gggtaaaaaa    6660
aacctcacta agaccagca gtgtgtggtg gctcctgcct gtaatcatgc ctgtaattcc    6720
agcacttagg gaggctatgg cgggagggtc gcttgagacc aggagttctt gaccagcctg    6780
gacaacaaag tgagacccca gctccacaaa aaaattttt tttaattacc tgggcatctt    6840
agcatatgcc tgtggtcaca gctatttggg aggcttaggt gggaggatcc cttgagccca    6900
ggagtttgag gctgcagtga gccatgatca taccactgca ctccagccca ggtgacagag    6960
tgagatcctg tctcaaaaaa agaaaaaaaa aactcaaaaa cccccaaat acatgggttt    7020
cataggatcc aaactactat gtgtgtatag atcctgtttt aaggaagtag atatataaaa    7080
atgagcattg ctaagttaaa tttggtaaat ttgccttata gaacaccctc gagtacgttt    7140
ccagtgagtg taaaatagga attgggatac ccaattcagt tgtactaaat tttcttttt    7200
tttttttttt ttgagacgga gtctcgctct gtcgcccagg ctggagtgca gtggcgggat    7260
ctcggctcac tgcaagctcc gcctcccggg ttcacgccat tctcctgcct cagcctccca    7320
agtagctggg actacaggcg cccgccacta cgcccggcta ttttttgta ttttagtag    7380
agacggggtt tcaccgtttt agccgggatg gtctcgatct cctgacctcg tgatccgccc    7440
gcctcggcct cccaaagtgc tgggattaca ggcgtgagcc accgcgcccg gcctagattt    7500
tctaagtaca cattgttttg gttatgtgtt ttgtgactac cacccccaaaa ctaataacca    7560
cctttttttt tttttgaga cagagtctca ctgtgtcacc caggctggag tgcagtggcg    7620
tgtgatcttg gctcactgca acctctgcct ctcggttca agtgattctc ctgcttcagc    7680
agctgggact acaggtgtgc accaccaagc ctggctaatt ttttgcattt tagtggagac    7740
ggggtttca ccatgttgac caggctgatc ttaaactctt gagctcaggc agtctgcctg    7800
```

```
cctcagcctc ctaaagtgct aggattacag gcgtgagcca ctgcgcccag cccaccgttt    7860
tatttgttca taattctgta gtccaggctg ggctcagcta ggcagttact ctgctggtgg    7920
tagtcgttgg tgtggctgcc ttttgctggc agctgggggc tgggcctgtc cctcttttt    7980 tttttctct tttctttttt cttttttttc aagatagggt ctcactctgt cacccaggtt    8040
ggagtgcagt ggcatgatct tagctcactg caacctctgc ctccagggct caagtgatcc    8100
tcccacctca gcctccccag tcgctgggac acaggcatg tgccaccatg cctggctaat    8160
tttttgtgta ttttgtagag acggggtttc gccatgttgc caggctggtc tcgaactcct    8220
gagctcaggc gatctactga cgttggcctc ccaaagtgtt gggatcacag gcatgaacca    8280
ccatgcctgg ccagggcctg ttcctcttta tgtggtctct ctagcagggt agctcagggc    8340
tttcaaaagt ataaaagcag aagtcagcag gcctttttaa ggcttcggcc tagaattgcc    8400
agtgtcgctt catcgacatt cagttagtta aagcaatcac aagcccagcc catttcaagg    8460
tgaaattact acagaggcat gaacaccatg aggtgtccat aggggccat cagcataaca    8520 cactgccaca tacatgcact cacttttttt ctttaaccta aagtgagatc catcagtagt    8580
acaggtagtt gttggcaaag cctcttgttc gttccttgta ctgagaccct agtctgtcac    8640
tgaggatttg gttttttgccc ttccagtgta tactctgaaa gagcgatgcc tccaggttgt    8700
ccggagccta gtcaagcctg agaattacag gagactggaa tcgtcaggt cgctctacga    8760 agatctggaa gaccacccaa atgtgcagaa agacctggag cggctgacac aggagcgcat    8820
tgcacatcaa cggatgggag attgaagatt tctgttgaaa cttacactgt ttcatctcag    8880
cttttgatgg tactgatgag tcttgatcta gatacaggac tggttccttc cttagtttca    8940
aagtgtctca ttctcagagt aaaataggca ccattgctta aaagaaagtt aactgacttc    9000
actaggcatt gtgatgttta ggggcaaaca tcacaaaatg taatttaatg cctgcccatt    9060
agagaagtat ttatcaggag aaggtggtgg catttttgct tcctagtaag tcaggacagc    9120
ttgtatgtaa ggaggtttat ataagtaatt cagtgggaat tgcagcatat cgtttaattt    9180
taagaaggca ttggcatctg ctttaatgg atgtataata catccattct acatccgtag    9240
cggttggtga cttgtctgcc tcctgctttg ggaagactga ggcatccgtg aggcagggac    9300
aagtctttct cctctttgag accccagtgc ctgcacatca tgagccttca gtcagggttt    9360
gtcagaggaa caaaccaggg gacactttgt tagaaagtgc ttagaggttc tgcctctatt    9420
tttgttgggg ggtgggagag gggaccttaa aatgtgtaca gtgaacaaat gtcttaaagg    9480
gaatcatttt tgtaggaagc atttttata attttctaag tcgtgcactt tctcggtcca    9540
ctcttgttga agtgctgttt tattactgtt tctaaactag gattgacatt ctacagttgt    9600
gataatagca ttttttgtaac ttgccatccg cacagaaaat acgagaaaat ctgcatgttt    9660
gattatagta ttaatggaca ataagttttt tgctaaatgt gagtatttct gttccttttt    9720
gtaaatatgt gacattcctg attgatttgg gtttttttgt tgttgttgtt ttgttttgtt    9780 ttgtttttt gggatggagk ctcactcttg tcacccaggc tggagtgcag tggcgccatc    9840
tcggctcact gcaacctctg cctcctgagt tcacgtaatc ctcctgagta gctgggatta    9900
caggtgcctg ccaccacgct ggccaatttt tgtactttta gtagagacag tgtttcgcca    9960
tgttggccag gctggtttca aactcctgac ctcaggtgat ccgcccacct cagcctccca   10020
aaatggtggg attacaggtg tgtgggccac cgtgcctggc tgattcagca ttttttatca   10080
ggcaggacca ggtggacttc cacctccagc ctctggtcct accaatggat tcatggagta   10140
gcctggactg tttcatagtt ttctaaatgt acaaattctt ataggctaga cttagattca   10200
```

-continued

```
ttaactcaaa ttcaatgctt ctatcagact cagttttttg taactaatag attttttttt    10260
ccacttttgt tctactcctt ccctaatagc tttttaaaaa aatctcccca gtagagaaac    10320
atttggaaaa gacagaaaac taaaaaggaa gaaaaaagat ccctattaga tacacttctt    10380
aaatacaatc acattaacat tttgagctat ttccttccag cctttttagg gcagattttg    10440
gttggttttt acatagttga gattgtactg ttcatacagt tttatacccct ttttcattta   10500
actttataac ttaaatattg ctctatgtta gtataagctt ttcacaaaca ttagtatagt    10560
ctccctttta taattaatgt ttgtgggtat ttcttggcat gcatctttaa ttccttatcc    10620
tagcctttgg gcacaattcc tgtgctcaaa aatgagagtg acggctggca tggtggctcc    10680
cgcctgtaat cccagtactt tgggaagcca aggtaagagg attgcttgag cccagaactt    10740
caagatgagc ctgggctcat agtgagaacc cgtctataca aaaattttt aaaaattagc     10800
atggcggcac acatctgtaa tcctagctac ttggcaggct gaggtgagaa gatcattgga    10860
gtttaggaat tggaggcggc agtgagtcat gagtatgccg ctgcactcca gcctggggga    10920
cagagcaaga ccctgcctca aaaaaaaaaa aaaaaaaat tcaggccggg aatggtggtt     10980
cacgcctgta atcccagcac tttgggggt cgaggtgggc agatcacctg aggtcaggag    11040
ttcgagacca gcctggccaa catggtaaaa cccccatttct actaaaaaat acaagaatta   11100
gctgggtgtg gtggcgcatg cctgtaatcc tagctactca ggaggctgag gcaggagaat    11160
cacttgaccc caggaggcga agattgcagt gagctgatat cgcaccattg tactccagcc    11220
tgtgtgacag agcaatactc ttgtcccaaa aaaaaaaaaa attcaaatca gagtgaagtg    11280
aatgagacac tccagttttc cttctactcc gaattttagc tcctcctttc aacattcaac    11340
aaaatagtct ttttttttt  tttttttttt ggggatggag tctccctctg ttgcccaggc    11400
tggagtgcag aggtgcgatc tctgctcact acaagctctg cctcccgagt tcaagtgatt    11460
ctcctggctc accctcctga gctgggatta caggcgcctg ccaccatgcc tggctaattt    11520
tgtgttttta gtggagacgg ggtttcacca tgttgtccag gatggtcttg atctcctgac    11580
cttgtgatcc acccacctca gcctcccaaa gtggtgggat tacaggtgtg agccaccgcg    11640
tccagccagc tttattattt ttttttaagct gtctttgtgt caaaatgata gttcatgctc    11700
ctcttgttaa aacctgcagg ccgagcacag tggctcatgc ctgtaatccc agcattttgg    11760
gagaccaagg cggatggatc acctgaggtc aggagctcaa gaccagcctg gctaacatgg    11820
tgaaacctca tctccactta aaatacaaaa attgccggcc gcggcggctc atgcctgtaa    11880
tcccagcact ttgggaggcc taggcgggtg gatcacgacg tcaggaaatc gagaccatcc    11940
tggctaacac gggtgaaacc ccgtctctat taaaaaatag aaaaaattag gcgggcgtgg    12000
tggtgagcgc ctgtagtccc agctactcga gagcctgagg caggagaatg gcatgaacct    12060
ggaaggtgga gcttgcagtg agctgagatg gtgccactgc actctaacct gggcgacaga    12120
gtgagactcc gtctcaaaaa aaaaacaaaa aaccaaaact tatccaggtg tggcggtggg    12180
cgcctgtgag gcaggcgaat ctcttgaacc cgggaggcgg aggttgcagt gagccaagat    12240
cacaccattg cactccagcc tgggaaacaa gagtgaaatt ccatctcaaa accaaatttt    12300
caaaaaaaaa acatgccgct tgagtactgt gttttttggtg ttgtccaagg aaaattaaaa    12360
cctgtagcat gaataatgtt tgttttcatt tcgaatcttg tgaatgtatt aaatatatcg    12420
ctcttaagag acggtgaagt tcctatttca agttttttt  gttttgtttt gttttttaagc    12480
tgttttttaa tacattaaat ggtgctgagt aaaggaaata ggcagggtgt gttgtgtggt    12540
```

-continued

```
gttttaacta ggcgcttctc tctcagagag ttttgaaacc tgtttacata aaggcccaag    12600
atgggaagga gatccaaaca taagccacca gcctcattcc aagtctcttc tctttccaac    12660
cctggatttt ttttttttat ttaacattgt ttcttttagc tttattttc ttataaaga     12720 aatgtatcac tataaaaaat tacacactac agaaaaatat taagaagaaa aacattcaca    12780
tcggaaacaa agtttttcc catgaaaaca gaacccaaaa gggtaagtgg ttagtatttc    12840
accagcaatt atgttgagaa taaggccagg cgaggtggct cacgcctgta atctcagcac    12900
tttgggaggc cagggcaggc agatcatctg aggtcaggag tttgagacca gcctggccaa    12960
catggtgaaa ccctatctct actaaaaatt aaaaaattag ctgggtgtgg tggcatgtac    13020
ctgtaatccc agctattcag gaggctgagg caggagaatt gcttgaacct gggaggcgga    13080
ggttgcagtg agctgagatt gcaccattgc actctagcct gggcaacgag tgaaactccg    13140
tctcaaaaga aaaaatata tatatataga gagagagaga gagagaatac cacagtgagg    13200
gcatgggcta gaaatcagtg cactaaggat atgaaataga tgtcaatgtg aacttttcgg    13260
atactttgac cctgggtctt tgtatcctct tcttagcacc tcagtcccac gctctgctag    13320
tcattggctt cctgataccc cttcaataca gactgagtat ccctaatcca aaatttcaa     13380 atccaaagca ctccaaaatc caagagtcca acgtgacgcc acaagtggaa agttccacat    13440
gcgagtactt aacacaaact tgtttcacgt gcaaaactgg ggaaaatatt gcttacaatt    13500
acctacagcc tgtgtctata aggtgtttat gaaactggtg ttatgatgta tatgttttct    13560
ttttttgttc ctggctcata actcccatag cccttgttac ggatgtgagc caccttgcct    13620
ggctgatttt taagttttt gtagagatgg ggtctcgctg tgttgccctg ctggttta      13680 actcctgggc tcaagcgatc ctcccacctt ggcctcccaa agccctggga ttacaggtga    13740
gattacaacc ctcatttcag agaaggtcct accccatacc ctgggggaag gaatggtgac    13800
atcataaagc ctcgttaaaa cccatgagga cagtggagag tgtcaggata gctgaactac    13860
gtgtagaggt tcctggaggg tggtgcgccc agggagggga cagaagctct gcgcccctta    13920 tcccataccct tggtgtacgc atctcttcat ctgtatcctt cgtaatatcc tttatgataa    13980
accaggtagg ccgggcgtgg tggctcacac atataatccc agcactttgg gaggctgagg    14040
taggaggatt gcttcagcct gggagttcaa gataacatca tagtgagatc ctgtctctac    14100
tagaaaaaaa aagaacaacc aggagtggtg gcgcatgctt gcagtcccag ctgttcagtt    14160
tgcactccag cctgggagac agagcaagac ctgctgtctc aaaaaaaaaa gactggtaaa    14220 cattttcac tgagttctgt tagccactcc agcaaattaa acccaaagcg aaggtggtgg     14280 gaacccaac ttgaagctgg ttggtcagaa gttctggagc cctaaacttg ctactggtgt     14340
gtgggtgggg gcagtcttgg ggactgaggc ctcaacctgc aggatctgat attatttcca    14400
gaaagatggt gttggaagtg aattagagga tacctaattg gtgttcactg cagaattgat    14460
tgcttgctcg ctctcgggaa gaaatctaca catttggaca cgaaagtgtt ctgggttggt    14520
attgtgttag tgtggaatct aga                                            14543
```

<210> SEQ ID NO 18
<211> LENGTH: 826
<212> TYPE: PRT
<213> ORGANISM: Homo sapiens

<400> SEQUENCE: 18

```
Met Glu Gly Ala Gly Gly Ala Asn Asp Lys Lys Lys Ile Ser Ser Glu
 1               5                  10                  15
```

```
Arg Arg Lys Glu Lys Ser Arg Asp Ala Ala Arg Ser Arg Arg Ser Lys
            20              25              30

Glu Ser Glu Val Phe Tyr Glu Leu Ala His Gln Leu Pro Leu Pro His
        35              40              45

Asn Val Ser Ser His Leu Asp Lys Ala Ser Val Met Arg Leu Thr Ile
    50              55              60

Ser Tyr Leu Arg Val Arg Lys Leu Leu Asp Ala Gly Asp Leu Asp Ile
65              70              75              80

Glu Asp Asp Met Lys Ala Gln Met Asn Cys Phe Tyr Leu Lys Ala Leu
            85              90              95

Asp Gly Phe Val Met Val Leu Thr Asp Asp Gly Asp Met Ile Tyr Ile
        100             105             110

Ser Asp Asn Val Asn Lys Tyr Met Gly Leu Thr Gln Phe Glu Leu Thr
    115             120             125

Gly His Ser Val Phe Asp Phe Thr His Pro Cys Asp His Glu Glu Met
130             135             140

Arg Glu Met Leu Thr His Arg Asn Gly Leu Val Lys Lys Gly Lys Glu
145             150             155             160

Gln Asn Thr Gln Arg Ser Phe Phe Leu Arg Met Lys Cys Thr Leu Thr
            165             170             175

Ser Arg Gly Arg Thr Met Asn Ile Lys Ser Ala Thr Trp Lys Val Leu
        180             185             190

His Cys Thr Gly His Ile His Val Tyr Asp Thr Asn Ser Asn Gln Pro
    195             200             205

Gln Cys Gly Tyr Lys Lys Pro Pro Met Thr Cys Leu Val Leu Ile Cys
210             215             220

Glu Pro Ile Pro His Pro Ser Asn Ile Glu Ile Pro Leu Asp Ser Lys
225             230             235             240

Thr Phe Leu Ser Arg His Ser Leu Asp Met Lys Phe Ser Tyr Cys Asp
            245             250             255

Glu Arg Ile Thr Glu Leu Met Gly Tyr Glu Pro Glu Glu Leu Leu Gly
        260             265             270

Arg Ser Ile Tyr Glu Tyr Tyr His Ala Leu Asp Ser Asp His Leu Thr
    275             280             285

Lys Thr His His Asp Met Phe Thr Lys Gly Gln Val Thr Thr Gly Gln
290             295             300

Tyr Arg Met Leu Ala Lys Arg Gly Gly Tyr Val Trp Val Glu Thr Gln
305             310             315             320

Ala Thr Val Ile Tyr Asn Thr Lys Asn Ser Gln Pro Gln Cys Ile Val
            325             330             335

Cys Val Asn Tyr Val Val Ser Gly Ile Ile Gln His Asp Leu Ile Phe
        340             345             350

Ser Leu Gln Gln Thr Glu Cys Val Leu Lys Pro Val Glu Ser Ser Asp
    355             360             365

Met Lys Met Thr Gln Leu Phe Thr Lys Val Glu Ser Glu Asp Thr Ser
370             375             380

Ser Leu Phe Asp Lys Leu Lys Lys Glu Pro Asp Ala Leu Thr Leu Leu
385             390             395             400

Ala Pro Ala Ala Gly Asp Thr Ile Ile Ser Leu Asp Phe Gly Ser Asn
            405             410             415

Asp Thr Glu Thr Asp Asp Gln Gln Leu Glu Glu Val Pro Leu Tyr Asn
        420             425             430

Asp Val Met Leu Pro Ser Pro Asn Glu Lys Leu Gln Asn Ile Asn Leu
```

-continued

```
                   435                 440                 445
Ala Met Ser Pro Leu Pro Thr Ala Glu Thr Pro Lys Pro Leu Arg Ser
    450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                485                 490                 495
Gln Thr Pro Ser Pro Ser Asp Gly Ser Thr Arg Gln Ser Ser Pro Glu
            500                 505                 510
Pro Asn Ser Pro Ser Glu Tyr Cys Phe Tyr Val Asp Ser Asp Met Val
    515                 520                 525
Asn Glu Phe Lys Leu Glu Leu Val Glu Lys Leu Phe Ala Glu Asp Thr
    530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Asp Phe Gln Leu Arg Ser
                565                 570                 575
Phe Asp Gln Leu Ser Pro Leu Glu Ser Ser Ser Ala Ser Pro Glu Ser
            580                 585                 590
Ala Ser Pro Gln Ser Thr Val Thr Val Phe Gln Gln Thr Gln Ile Gln
    595                 600                 605
Glu Pro Thr Ala Asn Ala Thr Thr Thr Thr Ala Thr Thr Asp Glu Leu
    610                 615                 620
Lys Thr Val Thr Lys Asp Arg Met Glu Asp Ile Lys Ile Leu Ile Ala
625                 630                 635                 640
Ser Pro Ser Pro Thr His Ile His Lys Glu Thr Thr Ser Ala Thr Ser
                645                 650                 655
Ser Pro Tyr Arg Asp Thr Gln Ser Arg Thr Ala Ser Pro Asn Arg Ala
            660                 665                 670
Gly Lys Gly Val Ile Glu Gln Thr Glu Lys Ser His Pro Arg Ser Pro
    675                 680                 685
Asn Val Leu Ser Val Ala Leu Ser Gln Arg Thr Thr Val Pro Glu Glu
    690                 695                 700
Glu Leu Asn Pro Lys Ile Leu Ala Leu Gln Asn Ala Gln Arg Lys Arg
705                 710                 715                 720
Lys Met Glu His Asp Gly Ser Leu Phe Gln Ala Val Gly Ile Gly Thr
                725                 730                 735
Leu Leu Gln Gln Pro Asp Asp His Ala Ala Thr Thr Ser Leu Ser Trp
            740                 745                 750
Lys Arg Val Lys Gly Cys Lys Ser Ser Glu Gln Asn Gly Met Glu Gln
    755                 760                 765
Lys Thr Ile Ile Leu Ile Pro Ser Asp Leu Ala Cys Arg Leu Leu Gly
    770                 775                 780
Gln Ser Met Asp Glu Ser Gly Leu Pro Gln Leu Thr Ser Tyr Asp Cys
785                 790                 795                 800
Glu Val Asn Ala Pro Ile Gln Gly Ser Arg Asn Leu Leu Gln Gly Glu
                805                 810                 815
Glu Leu Leu Arg Ala Leu Asp Gln Val Asn
            820                 825

<210> SEQ ID NO 19
<211> LENGTH: 3678
<212> TYPE: DNA
<213> ORGANISM: Homo sapiens
```

<400> SEQUENCE: 19

| | | | | |
|---|---|---|---|---|
| gtgaagacat | cgcggggacc | gattcaccat | ggagggcgcc | ggcggcgcga | acgacaagaa | 60 |
| aaagataagt | tctgaacgtc | gaaaagaaaa | gtctcgagat | gcagccagat | ctcggcgaag | 120 |
| taaagaatct | gaagtttttt | atgagcttgc | tcatcagttg | ccacttccac | ataatgtgag | 180 |
| ttcgcatctt | gataaggcct | ctgtgatgag | gcttaccatc | agctatttgc | gtgtgaggaa | 240 |
| acttctggat | gctggtgatt | tggatattga | agatgacatg | aaagcacaga | tgaattgctt | 300 |
| ttatttgaaa | gccttggatg | gttttgttat | ggttctcaca | gatgatggtg | acatgattta | 360 |
| catttctgat | aatgtgaaca | atacatggg | attaactcag | tttgaactaa | ctggacacag | 420 |
| tgtgtttgat | ttactcatc | catgtgacca | tgaggaaatg | agagaaatgc | ttacacacag | 480 |
| aaatggcctt | gtgaaaaagg | gtaaagaaca | aaacacacag | cgaagctttt | ttctcagaat | 540 |
| gaagtgtacc | ctaactagcc | gaggaagaac | tatgaacata | aagtctgcaa | catggaaggt | 600 |
| attgcactgc | acaggccaca | ttcacgtata | tgataccaac | agtaaccaac | ctcagtgtgg | 660 |
| gtataagaaa | ccacctatga | cctgcttggt | gctgatttgt | gaacccattc | ctcacccatc | 720 |
| aaatattgaa | attcctttag | atagcaagac | tttcctcagt | cgacacagcc | tggatatgaa | 780 |
| attttcttat | tgtgatgaaa | gaattaccga | attgatggga | tatgagccag | aagaactttt | 840 |
| aggccgctca | atttatgaat | attatcatgc | tttggactct | gatcatctga | ccaaaactca | 900 |
| tcatgatatg | tttactaaag | gacaagtcac | cacaggacag | tacaggatgc | ttgccaaaag | 960 |
| aggtggatat | gtctgggttg | aaactcaagc | aactgtcata | tataacacca | agaattctca | 1020 |
| accacagtgc | attgtatgtg | tgaattacgt | tgtgagtggt | attattcagc | acgacttgat | 1080 |
| tttctcccctt | caacaaacag | aatgtgtcct | taaaccggtt | gaatcttcag | atatgaaaat | 1140 |
| gactcagcta | ttcaccaaag | ttgaatcaga | agatacaagt | agcctctttg | acaaacttaa | 1200 |
| gaaggaacct | gatgctttaa | ctttgctggc | cccagccgct | ggagacacaa | tcatatcttt | 1260 |
| agattttggc | agcaacgaca | cagaaactga | tgaccagcaa | cttgaggaag | taccattata | 1320 |
| taatgatgta | atgctccctc | cacccaacga | aaaattacag | aatataaatt | tggcaatgtc | 1380 |
| tccattaccc | accgctgaaa | cgccaaagcc | acttcgaagt | agtgctgacc | ctgcactcaa | 1440 |
| tcaagaagtt | gcattaaaat | tagaaccaaa | tccagagtca | ctggaacttt | cttttaccat | 1500 |
| gcccccagatt | caggatcaga | cacctagtcc | ttccgatgga | agcactagac | aaagttcacc | 1560 |
| tgagcctaat | agtcccagtg | aatattgttt | ttatgtggat | agtgatatgg | tcaatgaatt | 1620 |
| caagttggaa | ttggtagaaa | aactttttgc | tgaagacaca | gaagcaaaga | acccatttc | 1680 |
| tactcaggac | acagatttag | acttggagat | gttagctccc | tatatcccaa | tggatgatga | 1740 |
| cttccagtta | cgttccttcg | atcagttgtc | accattagaa | agcagttccg | caagccctga | 1800 |
| aagcgcaagt | cctcaaagca | cagttacagt | attccagcag | actcaaatac | aagaacctac | 1860 |
| tgctaatgcc | accactacca | ctgccaccac | tgatgaatta | aaaacagtga | caaaagaccg | 1920 |
| tatggaagac | attaaaatat | tgattgcatc | tccatctcct | acccacatac | ataaagaaac | 1980 |
| tactagtgcc | acatcatcac | catatagaga | tactcaaagt | cggacagcct | caccaaacag | 2040 |
| agcaggaaaa | ggagtcatag | aacagacaga | aaaatctcat | ccaagaagcc | ctaacgtgtt | 2100 |
| atctgtcgct | ttgagtcaaa | gaactacagt | tcctgaggaa | gaactaaatc | caaagatact | 2160 |
| agctttgcag | aatgctcaga | gaaagcgaaa | atggaacat | gatggttcac | ttttcaagc | 2220 |
| agtaggaatt | ggaacattat | tacagcagcc | agacgatcat | gcagctacta | catcactttc | 2280 |

-continued

```
ttggaaacgt gtaaaaggat gcaaatctag tgaacagaat ggaatggagc aaaagacaat    2340
tattttaata ccctctgatt tagcatgtag actgctgggg caatcaatgg atgaaagtgg    2400
attaccacag ctgaccagtt atgattgtga agttaatgct cctatacaag gcagcagaaa    2460
cctactgcag ggtgaagaat tactcagagc tttggatcaa gttaactgag cttttttctta   2520
atttcattcc ttttttttgga cactggtggc tcactaccta aagcagtcta tttatatttt   2580
ctacatctaa ttttagaagc ctggctacaa tactgcacaa acttggttag ttcaattttt    2640
gatcccctttt ctacttaatt tacattaatg ctcttttttta gtatgttctt taatgctgga   2700
tcacagacag ctcattttct cagttttttg gtatttaaac cattgcattg cagtagcatc    2760
attttaaaaa atgcacctttt ttatttattt attttttggct agggagttta tcccttttttc 2820
gaattatttt taagaagatg ccaatataat ttttgtaaga aggcagtaac ctttcatcat    2880
gatcataggc agttgaaaaa ttttttacacc tttttttttca cattttacat aaataataat  2940
gctttgccag cagtacgtgg tagccacaat tgcacaatat attttcttaa aaaataccag    3000
cagttactca tggaatatat tctgcgtttta taaaactagt ttttaagaag aattttttt    3060
tggcctatga aattgttaaa cctggaacat gacattgtta atcatataat aatgattctt    3120
aaatgctgta tggtttatta tttaaatggg taaagccatt tacataatat agaaagatat    3180
gcatatatct agaaggtatg tggcatttat ttggataaaa ttctcaattc agagaaatca    3240
tctgatgttt ctatagtcac tttgccagct caaaagaaaa caatacccta tgtagttgtg    3300
gaagtttatg ctaatattgt gtaactgata ttaaacctaa atgttctgcc taccctgttg    3360
gtataaagat attttgagca gactgtaaac aagaaaaaaa aaatcatgca ttcttagcaa    3420
aattgcctag tatgttaatt tgctcaaaat acaatgtttg attttatgca ctttgtcgct    3480
attaacatcc ttttttttcat gtagatttca ataattgagt aattttagaa gcattatttt   3540
aggaatatat agttgtcaca gtaaatatct tgttttttct atgtacattg tacaaatttt    3600
tcattccttt tgctctttgt ggttggatct aacactaact gtattgtttt gttacatcaa    3660
ataaacatct tctgtgga                                                  3678
```

INTERACTION BETWEEN THE VHL TUMOR SUPPRESSOR AND HYPOXIA INDUCIBLE FACTOR, AND ASSAY METHODS RELATING THERETO

The present invention relates to the finding of a novel interaction between the VHL and HIF proteins, assays based upon this interaction and novel compounds obtainable by such assay methods.

BACKGROUND TO THE INVENTION

Enhanced glucose metabolism and angiogenesis are classical features of cancer involving up-regulation of genes which are normally inducible by hypoxia. In addition to stimulation by the hypoxic microenvironment, genetic alterations contribute to these effects. A striking example is von Hippel-Lindau (VHL) disease, a hereditary human cancer syndrome predisposing to highly angiogenic tumours, particularly of the central nervous system, kidney, retina and adrenal glands.

VHL syndrome is caused by germline mutations in the VHL tumour suppressor, and VHL tumours are associated with loss or mutation of the remaining wild-type allele. VHL is also inactivated in —80% of sporadic clear cell renal carcinomas (RCC), the predominant form of kidney cancer. The ability of RCC cells to form tumours in nude mice can be abrogated by introduction of wild-type VHL.

VHL-associated tumours are highly vascularized, and this supports the current model that VHL negatively regulates the production of hypoxia-inducible factors such as the angiogenic vascular endothelial growth factor (VEGF). $VHL^{-/-}$ tumour cells have high levels of these factors, and reintroduction of VHL down-regulates them under normoxic conditions. The mechanism of this VHL activity is not well understood.

Stebbins et al (Science, 1999, 284; 55–61) report that the VHL protein forms a complex with the Elongin C and Elongin B proteins, and that the complex (the VCB complex) is formed by a direct interaction of VHL and Elongin C, with a second interaction between the Elongin C and B proteins. The interface of VHL which interacts with Elongin C contains a number of residues which are commonly mutated in VHL syndrome. The authors also found a second domain of VHL, not involved in binding Elongin C, which they speculate may correspond to another macromolecular binding site of VHL.

Hypoxia inducible factor-1 (HIF-1) plays a key role in a wide variety of cellular responses to hypoxia, including the regulation of genes involved in energy metabolism, vasomotor control, angiogenesis, proliferation, apoptosis and matrix remodelling. HIF is a heterodimer of an HIF α subunit and the aryl hydrocarbon receptor nuclear translocator (ARNT) protein, a member of the PAS superfamily of basic helix-loop-helix proteins. A major regulatory mechanism involves proteolysis of HIF α subunits which are rapidly degraded by the proteasome in normoxia but stabilised by hypoxia.

DISCLOSURE OF THE INVENTION

Although it has been proposed in the past that the VHL protein may mediate its effect via the destabilisation of hypoxia-regulated mRNA transcripts, we have surprisingly found that this protein has a direct interaction with HIF α subunits. While not wishing to be bound by any one theory, it is believed that the formation of a VHL-α subunit complex targets the α subunits for destruction, possibly by the association of the complex with the Elongin B subunit, which has homology to ubiquitin.

Modulation of the interaction of VHL with HIF α subunits has a variety of uses. Blocking the interaction may facilitate cell cycle progression and the production of a number of proteins which promote angiogenesis and/or promote cellular survival or cellular function in hypoxia, a desirable outcome in the treatment of certain clinical conditions, particularly ischaemic conditions such as coronary, cerebral and vascular insufficiency.

Thus in a first aspect the present invention provides an assay for a modulator of VHL-HIF α subunit interaction, which comprises:

a) bringing into contact a VHL protein, a HIF α subunit protein and a putative modulator compound under conditions where the VHL protein and the HIF α subunit protein, in the absence of modulator, are capable of forming a complex; and b) measuring the degree of inhibition of complex formation caused by said modulator compound.

The present invention further provides an assay for a modulator of VHL-HIF α subunit interaction, which comprises:

a) bringing into contact a VHL protein, a HIF α subunit protein and a putative modulator compound under conditions where the VHL protein and the HIF α subunit protein, in the absence of modulator, are capable of forming a complex;

b) providing an HIF response element to which the HIF α subunit protein is capable of binding and/or transcriptionally activating; and c) measuring the degree of modulation of binding of the α subunit to, or transcriptional activation of, the response element caused by said modulator compound.

In a further aspect, the invention provides compounds obtainable by such an assays for example peptide compounds based on the portions of VHL or HIF α subunit which interact with each other.

The assay of the invention may be performed in vitro using isolated, purified or partially purified VHL and HIF α subunit proteins, or in cell free or cellular systems in which case the assay may optionally be performed in the presence of a factor which promotes a normoxic cellular state, such as the presence of oxygen (e.g. about 21% $O_2$, 5% $CO_2$, balance $N_2$) and/or the presence of hydrogen peroxide at about 50–200 µM.

BRIEF DESCRIPTION OF THE DRAWINGS

FIGS. 1A–1F show the GenBank entry for AF010238 containing SEQ ID NO: 16 and SEQ ID NO: 17.

FIGS. 2A–2C show the GenBank entry for U22431, including SEQ ID NO: 18 and SEQ ID NO: 19.

DETAILED DESCRIPTION OF THE INVENTION

VHL

The VHL may be any suitable mammalian VHL, particularly human VHL. Human VHL has been cloned and sources of the gene can be readily identified by those of skill in the art. Its sequence is available as Genbank accession numbers AF010238 and L15409. Other mammalian VHLs are also available, such as murine VHL (accession number U12570) and rat (accession numbers U14746 and S80345). Non-mammalian homologues include the VHL-like protein of C. elegans, accession number F08G12.4. VHL gene sequences may also be obtained by routine cloning techniques, for example by using all or part of the human VHL gene sequence as a probe to recover and to determine the sequence of the VHL gene in other species. A wide variety of techniques are available for this, for example PCR amplification and cloning of the gene using a suitable source of mRNA (e.g. from an embryo or a liver cell), obtaining a cDNA library from a mammalian, vertebrate, invertebrate or fungal source, e.g. a cDNA library from one of the above-mentioned sources, probing said library with a polynucleotide of the invention under stringent conditions, and recovering a cDNA encoding all or part of the VHL protein of that mammal. Suitable stringent conditions include hybridization on a solid support (filter) overnight incubation at 42° C. in a solution containing 50% formamide, 5×SSC (750 mM NaCl, 75 mM sodium citrate), 50 mM sodium phosphate (pH7.6), 5×Denhardt's solution, 10% dextran sulphate and 20 µg/ml salmon sperm DNA, followed by washing in 0.03M sodium chloride and 0.03M sodium citrate (i.e. 0.2×SSC) at from about 50° C. to about 60° C.). Where a partial cDNA is obtained, the full length coding sequence may be determined by primer extension techniques.

A further approach is to use the above-identified sequences as query sequences to search databases for homologous gene sequences or partial gene sequences (particularly ESTS). Matches identified may be examined and where an actual or putative VHL sequence is found, the gene recovered by physical cloning using, for example PCR and RACE-PCR based on the sequence of the match.

Although wild-type VHL is preferred mutants and variants of VHL which still retain the ability to interact directly with the HIF α subunit may also be used. Examples of VHL mutants are well known in the art and include mutants described by Stebbings et al (ibid) which have changes to the Elongin C interacting interface.

Mutants and other variants will generally be based on wild-type mammalian VHLs and have a degree of amino acid identity which is desirably at least 70%, preferably at least 80%, 90%, 95% or even 98% homologous to a wild type mammalian VHL, preferably to human VHL.

It is not necessary to use the entire VHL proteins (including their mutants and other variants) for assays of the invention. Fragments of the VHL maybe used provided such fragments retain the ability to interact with the target domain of the HIF α subunit. Optionally, the fragment may include the Elongin C interacting interface domain. Fragments of VHL may be generated in any suitable way known to those of skill in the art. Suitable ways include, but are not limited to, recombinant expression of a fragment of the DNA encoding the VHL. Such fragments may be generated by taking DNA encoding the VHL, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments of the VHL (up to about 20 or 30 amino acids) may also be generated using peptide synthesis methods which are well known in the art. Generally fragments will be at least 40, preferably at least 50, 60, 70, 80 or 100 amino acids in size.

Particularly preferred fragments include those which are based upon the beta domain located within the fragment 63–156 of the 213 amino acid human VHL protein, or the equivalent domain in other variants. In a preferred embodiment, such domains will have at least 70%, preferably 80%, 90%, 95% or even 98% degree of sequence identity to the 64–156 fragment of human VHL. Fragments of this region and its variants may be used. These fragments may be 15–80 amino acids in length, for example from 20 to 80, such as 30–60 amino acids in length. Fragments may include the regions 71–90 or 90–109 of human VHL or their equivalents in the above described variants. Desirably, the wild-type sequence of the beta domain is retained.

One fragment which may be used is that in which up to 53 of the N-terminal residues, e.g. from 1 to n wherein n is an integer of from 2 to 53, have been deleted, the rest of the protein being wild-type.

The ability of suitable fragments to bind to the HIF α subunit (or fragment thereof) may be tested using routine procedures such as those described in the accompanying examples relating to intact VHL. Reference herein to a VHL protein includes the above mentioned mutants and fragments which are functionally able to bind the HIF α subunit unless the context is explicitly to the contrary.

HIF α Subunit Protein

The HIF α subunit protein may be any human or other mammalian protein, or fragment thereof which has the ability to bind to a wild type full length VHL protein, such that the binding is able, in a normoxic cellular environment, to target the α subunit for destruction.

A number of HIF α subunit proteins have been cloned. These include HIF-1α, the sequence of which is available as Genbank accession number U22431, HIF-2α, available as Genbank accession number U81984 and HIF-3α, available as Genbank accession numbers AC007193 and AC079154. These are all human HIF α subunit proteins. HIF α subunit proteins from other species, including murine HIF-1α (accession numbers AF003695, U59496 and X95580), rat HIF-1α (accession number Y09507), murine HIF-2α (accession numbers U81983 and D89787) and murine HIF-3α (accession number AF060194). Other mammalian, vertebrate, invertebrate or fungal homologues may be obtained by techniques similar to those described above for obtaining VHL homologues.

There are a number of common structural features found in the two HIF α subunit proteins identified to date. Some of these features are identified in O'Rourke et al (1999, J. Biol. Chem., 274; 2060–2071). Some of these features are involved in the transactivation functions of the HIF α subunit proteins, and such domains will be required in assays of the invention which are based on the ability of HIF-1 to bind to and activate hypoxia response elements.

Our data indicate that HIF-1α residues 344–698, more particularly 549–652 and even more particularly the N-terminal region thereof (549–572) interact with the VHL protein. Such a region, or its equivalents in other HIF α subunit proteins, is desirably present. However the data do not exclude the presence of other domains which interact with the VHL protein.

Variants of the above HIF α subunits may be used, such as synthetic variants which have at least 45% amino acid identity to a naturally occurring HIF α subunit (particularly a human HIF α subunit), preferably at least 50%, 60%, 70%, 80%, 90%, 95% or 98% identity.

The assays of the invention preferably use the same mammalian source HIF α subunit as the VHL.

Fragments of the HIF α subunit protein and its variants may be used, provided that said fragments retain the ability to interact with a wild-type VHL, preferably wild-type human VHL. Such fragments are desirably at least 20, preferably at least 40, 50, 75, 100, 200, 250 or 400 amino acids in size. Desirably such fragments include the region 549–572 found in human HIF-1α or its equivalent regions in other HIF α subunit proteins, e.g. 517–542 of HIF-2α. Optionally the fragments also include one or more domains of the protein responsible for transactivation. Reference herein to a HIF α subunit protein includes the above mentioned mutants and fragments which are functionally able to bind VHL protein unless the context is explicitly to the contrary.

Amino Acid Identity

The percentage homology (also referred to as identity) of DNA and amino acid sequences can be calculated using commercially available algorithms. The following programs (provided by the National Center for Biotechnology Information) may be used to determine homologies: BLAST, gapped BLAST and PSI-BLAST, which may be used with default parameters. The algorithm GAP (Genetics Computer Group, Madison, Wis.) uses the Needleman and Wunsch algorithm to align two complete sequences that maximizes the number of matches and minimizes the number of gaps. Generally, the default parameters are used, with a gap creation penalty=12 and gap extension penalty=4. Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions.

Where default parameters or other features of these programs are subject to revision, it is to be understood that reference to the programs and their parameters are as of the priority date of the instant application.

Assay Formats

One assay format which is widely used in the art to study the interaction of two proteins is a two-hybrid assay. This assay may be adapted for use in the present invention. A two-hybrid assay comprises the expression in a host cell of the two proteins, one being a fusion protein comprising a DNA binding domain (DBD) such as the yeast GAL4 binding domain, and the other being a fusion protein comprising an activation domain, such as that from GAL4 or VP16. In such a case the host cell (which again may be bacterial, yeast, insect or mammalian, particularly yeast or mammalian) will carry a reporter gene construct with a promoter comprising a DNA binding elements compatible with the DBD. The reporter gene may be a reporter gene such as chloramphenicol acetyl transferase, luciferase, green fluorescent protein (GFP) and β-galactosidase, with luciferase being particularly preferred.

Two-hybrid assays may be in accordance with those disclosed by Fields and Song, 1989, Nature 340; 245–246. In such an assay the DNA binding domain (DBD) and the transcriptional activation domain (TAD) of the yeast GAL4 transcription factor are fused to the first and second molecules respectively whose interaction is to be investigated. A functional GAL4 transcription factor is restored only when two molecules of interest interact. Thus, interaction of the molecules may be measured by the use of a reporter gene operably linked to a GAL4 DNA binding site which is capable of activating transcription of said reporter gene.

In the case of the present invention, where the HIF α subunit protein being used includes a transactivation domain then the VHL protein is preferably fused to the DNA binding domain and the HIF α subunit protein may be used without extraneous TAD sequences.

Thus two hybrid assays may be performed in the presence of a potential modulator compound and the effect of the modulator will be reflected in the change in transcription level of the reporter gene construct compared to the transcription level in the absence of a modulator.

Host cells in which the two-hybrid assay may be conducted include mammalian, insect and yeast cells.

A similar assay may be conducted based on the activation of a hypoxia response element, which is found in a variety of genes as described in the accompanying examples. Such assays generally utilise such an element operably linked to a reporter gene, such as those mentioned above for two-hybrid assays. Such assays are generally conducted in cells or cell-free systems which provide for the targeted removal of the HIF α subunit protein in the presence of the VHL protein. Constructs providing for expression of a reporter and one or both of an HIF α subunit and VHL are introduced into the cell (e.g. a mammalian cell) and the production of the reporter is examined in the presence and absence of a modulator.

The interaction of the HIF α subunit to its cognate HRE may also be examined directly, for example using an EMSA (electrophoretic mobility shift assay).

Another assay format measures directly the interaction between VHL and the HIF α subunit by labelling one of these proteins with a detectable label and bringing it into contact with the other protein which has been optionally immobilised on a solid support, either prior to or after proteins have been brought into contact with each other. Suitable detectable labels include $^{35}$S-methionine which maybe incorporated into recombinantly produced proteins, and tags such as an HA tag, GST or histidine. The recombinantly produced protein may also be expressed as a fusion protein containing an epitope which can be labelled with an antibody. Alternatively, an antibody against the VHL and/or HIF α subunit can be obtained using conventional methodology.

The protein which is optionally immobilized on a solid support may be immobilized using an antibody against that protein bound to a solid support or via other technologies which are known per se.

Alternatively, the interaction of the proteins may be measured by immunoprecipitation of one followed by immunological detection of the other, e.g. by western blotting or electrophoretic mobility or detectably labelled proteins.

In a further alternative mode, the one of the VHL and the HIF α subunit may be labelled with a fluorescent donor moiety and the other labelled with an acceptor which is capable of reducing the emission from the donor. This allows an assay according to the invention to be conducted by fluorescence resonance energy transfer (FRET). In this mode, the fluorescence signal of the donor will be altered when the VHL and an HIF α subunit interact. The presence of a candidate modulator compound which modulates the interaction will increase or decrease the amount of unaltered fluorescence signal of the donor.

FRET is a technique known per se in the art and thus the precise donor and acceptor molecules and the means by which they are linked to the VHL and an HIF α subunit may be accomplished by reference to the literature.

Suitable fluorescent donor moieties are those capable of transferring fluorogenic energy to another fluorogenic molecule or part of a compound and include, but are not limited to, coumarins and related dyes such as fluoresceins, and suitable acceptors include, but are not limited to, coumarins and related fluorophlores, and the like.

Another technique which may be used is a scintillation proximity assay (reagents and instructions available from Amersham Pharmacia Biotech) in which a target compound (i.e. for this invention VHL, HIF α or ubiquitin) is held on (or in the course of the assay attached to) a bead having a signalling compound which scintillates when activated by radioactivity emitted by a radiolabel attached to a target-binding molecule (i.e. for this invention another of the VHL, HIF α and ubiquitin).

The precise format of the assays of the invention may be varied by those of skill in the art using routine skill and knowledge. In the in vitro assays of the invention, the amount of VHL, HIF α subunit and, where required, further components, may be varied depending upon the scale of the assay. In general, the person of skill in the art will select relatively equimolar amounts of the two components, say from 1:10 to 100:1, preferably from 1:1 to 10:1, molar ratio of VHL to HIF α subunit. However there may be particular assay formats which can be practised outside this range.

Where assays of the invention are performed within cells, the cells may be treated to provide or enhance a normoxic environment. By "normoxic" it is meant levels of oxygen similar to those found in normal air, e.g. about 21% $O_2$ and 5% $CO_2$, the balance being nitrogen. Of course, these exact proportions do not have to be used, and may be varied independently of each other. Generally a range of from 10–30% oxygen, 1–10% $CO_2$ and a balance of nitrogen or other relatively inert and non-toxic gas may be used. Normoxia may be induced or enhanced in cells, for example by culturing the cells in the presence of hydrogen peroxide as described above.

Alternatively, or by way of controls, cells may also be cultured under hypoxic conditions. By "hypoxic" it is meant an environment with reduced levels of oxygen. Most preferably oxygen levels in cell culture will be 0.1. to 1.0% for the provision of a hypoxic state. Hypoxia may be induced in cells simply by culturing the cells in the presence of lowered oxygen levels. The cells may also be treated with compounds which mimic hypoxia and cause up-regulation of HIF α subunit expression. Such compounds include iron chelators, cobalt (II), nickel (II) or manganese (II), all of which may be used at a concentration of 20 to 500 $\mu$M, such as 100 $\mu$M. Iron chelators include desferrioxamine, O-phenanthroline or hydroxypyridinones (e.g. 1,2-diethyl-3-hydroxypyridin-4-one (CP94) or 1,2-dimethyl-3-hydroxypyridin-4-one (CP20)).

Cells in which assays of the invention may be preformed include eukaryotic cells, such as yeast, insect, mammalian, primate and human cells. Mammalian cells may be primary cells or transformed cells, including tumour cell lines. The cells may be modified to express or not to express other proteins which are known to interact with HIF α subunit proteins and VHL protein, for example Elongin C and Elongin B proteins in the case of VHL and ARNT protein in the case of HIF α subunit protein. In assays which included an HRE based in cells and cell free systems, a preferred assay utilises a reporter gene as discussed above and illustrated in the accompanying examples. Such assays may be of a two-hybrid type as discussed above. A more complex assay may be provided which may determine DNA binding or transcription of endogenous HIF-responsive genes. Such an assay will require the presence of, or provision of, factors including HIF-1β/ARNT and Elongins B and C.

In cell free systems such additional proteins may be included, for example by being provided by expression from suitable recombinant expression vectors.

In the assays of the invention performed in cells, it will be desirable to achieve sufficient expression of VHL to recruit sufficient HIF α subunit to a complex such that the effect of a putative modulator compound may be measured. The level of expression of VHL and HIF α subunit may be varied within fairly wide limits, so that the intracellular levels of the two may vary by a wide ratio, for example from 1:10 to 1000:1, preferably 1:1 to 100:1, molar ratio of VHL to HIF α subunit.

Our results confirm that binding of VHL to the HIF α subunit initiates destruction of the resulting complex via ubiquitylation, and thus assays of the invention may also be performed in which the measurement of the degree of inhibition of complex formation is determined by measuring the amount of HIF-1α ubiquitylation. Such an assay may be performed in cells in culture or in a cell free assay system, in which a source of ubiquitin is provided.

In another embodiment, we have also found that when HIF-1α is synthesised by recombinant means in the presence of iron ions, this enhances the binding of this protein to VHL. Thus assays of the invention may be performed by producing the HIF α subunit recombinantly in the presence of iron ions, e.g. from 10 to 200 $\mu$M, such as 100 $\mu$M Fe 2+ and/or 3+, and using the HIF α subunit thus produced in the above-described assays. By "recombinantly", this includes expression in host cells (such as those mentioned below) as well as production in a cell free system such as a reticulocyte lysate. Conversely, the production of the HIF α subunit in the presence of an iron chelator, cobalt (II), nickel (II) or manganese (II) diminishes the interaction of the HIF α subunit with VHL.

It thus appears that the environment in which HIF α is produced can effect the ability of this protein to interact with VHL. Thus in an embodiment of the invention related to the above, there is provided an assay for a modulator of HIF-α-dependent gene expression which comprises *producing a HIF α subunit in the presence of a putative modulator compound, and determining whether the presence of the modulator alters the ability of the HIF α subunit to form a complex with VHL.

In a further part of this aspect of the invention, the invention also provides an assay for a modulator of HIF-α-dependent gene expression which comprises producing a HIF α subunit in the presence of an iron ion, an iron chelator, cobalt (II), nickel (II) or manganese (II) and a putative modulator compound, and determining whether the presence of the modulator alters the ability of the HIF α subunit to form a complex with VHL.

The HIF α subunit may be produced in lysates or in recombinant expression systems such as in bacterial, yeast, insect or mammalian host cells. Expression systems for these and other cell types are well known, e.g the baculovirus expression system for the production of proteins in insect host cells.

Modulator Compounds

The amount of putative modulator compound which may be added to an assay of the invention will normally be determined by trial and error depending upon the type of compound used. Typically, from about 0.01 to 100 nM concentrations of putative modulator compound may be used, for example from 0.1 to 10 nM. Modulator compounds may be those which either agonise or antagonise the interaction. Antagonists (inhibitors) of the interaction are particularly desirable.

Modulator compounds which may be used may be natural or synthetic chemical compounds used in drug screening programmes. Extracts of plants which contain several characterised or uncharacterised components may also be used. Modulators which are putative inhibitor compounds can be derived from the VHL and HIF α subunit protein sequences.

Peptide fragments of from 5 to 40 amino acids, for example from 6 to 10 amino acids from the region of VHL and HIF α subunit which are responsible for the interaction between these proteins may be tested for their ability to disrupt this interaction. Antibodies directed to the site of interaction in either protein form a further class of putative inhibitor compounds. Candidate inhibitor antibodies nay be characterised and their binding regions determined to provide single chain antibodies and fragments thereof which are responsible for disrupting the interaction between VHL and the HIF α subunit.

A particular class of peptide compounds will be those based upon the region 344–698, such as 549–652, particularly 549–572 of human HIF-1α or the equivalent region of other HIF α subunit proteins. Such peptides are preferably from5 to 50 amino acids in size.

Thus in a further aspect the invention provides an isolated polypeptide which consists of from 5 to 50 amino acids whose sequence is found in region 344–698, such as 549–652, particularly 549–572 of human HIF-1α

Within the region 549–572 HIF α subunit proteins are highly conserved. Indeed, both human and murine HIF-1α are identical over the region 551–572 and human and murine HIF-2α (which are differ only by an N-S substitution from each other in this region) are very similar, with one substitution (T-N/S) and three insertions compared to HIF-1α. All these proteins share the motif: LAPYIPMD (SEQ ID NO:1) (written here in the conventional 1-letter code in the N to C terminal direction) and this motif or variants of it comprising from 1 to 3, preferably 1 or 2 substitutions may be provided as a polypeptide of the present invention. Substitutions may be conserved substitutions as described herein.

An example of such sequences include:

| | |
|---|---|
| LAPYISMD (found in human HIF-3α) | SEQ ID NO:2; |
| LLPYIPMD; | SEQ ID NO:3 |
| LVPYIPMD; | SEQ ID NO:4 |
| IAPYIPMD; | SEQ ID NO:5 |
| IAPYIPME; | SEQ ID NO:6, | and

LVPYISMD　　　　　　　　　　　　SEQ ID NO:7.

Thus a peptide of the invention may comprise from 8 to 50, such as from 8 to 15 amino acids which are characterised by the above sequences. We have found that peptides based upon these sequences is capable of inhibiting the interaction of the VHL and HIF α proteins.

Further peptides of the invention include:

DLDLEMLAPYIPMDDDFQL　　　　　(SEQ ID NO:8);

variants thereof in which there are from 1 to 4, such as from 1 to 3, e.g. 1 or 2 substitutions (the term "substitution" includes substitution by no amino acids (i.e. a deletion)), e.g. a variant in which the SEQ ID NO:1 region of SEQ ID NO:8 is replaced by any one of SEQ ID NO:2 to SEQ ID NO:7; and polypeptides consisting of from 20 to 50 amino acids which contain SEQ ID NO:8.

A particular polypeptide of the latter type is:

PFSTQDTDLDLEMLAPYIPMDDDFQLRSF
　　DQLSP　　　　　　　　　　　　(SEQ ID NO:9);

or variants thereof as defined for SEQ ID NO:8 above; and polypeptides consisting of from 35 to 50 amino acids which contain SEQ ID NO:9.

Similarly, peptides based on the mutational clusters found in the VHL regions 71–90 and 90–109 described above are provided as a further aspect of the invention, particularly peptides which have these sequences of human VHL or are variants of it comprising from 1 to 3, preferably 1 or 2 substitutions, particularly conserved substitutions as described herein.

The amino acids of such polypeptides may be substituted, for example from 1 to 5 amino acids (subject to a maximum of 20% of the total size of the peptide) to provide variant polypeptides which form a further aspect of the invention.

Substitutions may include conserved substitutions, for example according to the following table, where amino acids on the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R H |
| AROMATIC | | F W Y |

Alternatively, any amino acid may be replaced by a small aliphatic amino acid, preferably glycine or alanine.

In addition, deletions and insertions (e.g. from 1 to 5 subject to a maximum of 20% of the amino acids) may also be made. Insertions are preferably insertions of small aliphatic amino acids, such as glycine or alanine, although other insertions are not excluded.

Variant polypeptides may also modified in any of the ways described herein for polypeptides of the invention. This includes for example "reverse" C-terminal to N-terminal sequences, synthetic amino acids, modified side chains and labelling.

Polypeptides maybe provided in the form of molecules which contain multiple copies of the peptide (or mixtures of peptides). For example, the amino group of the side chain of lysine may be Used as an attachment point for the carboxy terminus of an amino acid. Thus two amino acids may be joined to lysine via carbonyl linkages, leading to a branched structure which may in turn be branched one or more times. By way of example, four copies of a peptide of the invention may be joined to such a multiple antigen peptide (MAP), such as a MAP of the structure $Pep_4$-$Lys_2$-Lys-X, where Pep is a peptide from the HIF α subunit region or variant thereof (optionally in the form of a heterologous fusion), Lys is lysine and X is a terminal group such as β-alanine which provides for joining of the MAP core to a solid support such as a resin for synthesis of the $Pep_4$-MAP peptide and which may be removed from the support once synthesis is complete.

Other multiple peptide structures may be obtained using the MAP cores described in: Lu et al, 1991, Mol Immunol, 28, 623–30; Briand et al, 1992, J Immunol Methods, 156, 255–65; Ahlborg, 1995, J Immunol Methods, 179, 269–75.

Where multimers of the invention are provided, they may comprise different peptides of the invention or be multimers of the same peptide.

Except where specified to the contrary, the polypeptide sequences described herein are shown in the conventional 1-letter code and in the N-terminal to C-terminal orientation. The amino acid sequence of polypeptides of the invention may also be modified to include non-naturally-occurring amino acids or to increase the stability of the compound in vivo. When the compounds are produced by synthetic means, such amino acids may be introduced during production. The compound may also be modified following either synthetic or recombinant production.

Polypeptides of the invention may also be made synthetically using D-amino acids. In such cases, the amino acids will be linked in a reverse sequence in the C to N orientation. This is conventional in the art for producing such peptides.

A number of side-chain modifications for amino acids are known in the art and may be made to the side chains of polypeptides of the present invention. Such modifications include for example, modifications of amino groups by reductive alkylation by reaction with an aldehyde followed by reduction with $NaBH_4$, amidination with methylacetimidate or acylation with acetic anhydride.

The guanidino groups of arginine residues may be modified by the formation of heterocyclic condensation products with reagents such as 2,3-butanedione or glyoxal. Sulphydryl groups may be modified by methods such as carboxymethylation, tryptophan residues may be modified by oxidation or alkylation of the indole ring and the imidazole ring of histidine residues may be modified by alkylation.

The carboxy terminus and any other carboxy side chains may be blocked in the form of an ester group, e.g. a $C_{1-6}$alkyl ester.

The above examples of modifications to amino acids are not exhaustive. Those of skill in the art may modify amino acid side chains where desired using chemistry known per se in the art.

Polypeptides may be made synthetically or recombinantly, using techniques which are widely available in the art. Synthetic production generally involves step-wise addition of individual amino acid residues to a reaction vessel in which a polypeptide of a desired sequence is being made. Examples of recombinant techniques are described below.

Polypeptides may be in a substantially isolated form. It will be understood that the polypeptide may be mixed with carriers or diluents which will not interfere with the intended purpose of the polypeptide and still be regarded as substantially isolated. A polypeptide may also be in a substantially purified form, in which case it will generally comprise the polypeptide in a preparation in which more than 90%, e.g. 95%, 98% or 99% of the polypeptide in the preparation is the polypeptide based on the HIF α subunit sequence.

Peptide antagonists of the interaction of VHL with an HIF α subunit may be linked, at the C- or N-terminal, to a member of the class of sequences which are membrane translocation sequences capable of directing a polypeptide through the membrane of a eukaryotic cell. Example of such polypeptides include the HSV-1 VP22 protein (Elliot, G. and O'Hare, P. (1997) Cell 88, 223–233), the HIV Tat protein (for example residues 1–72 or 37–72 (Fawell, S., et al, (1994) Proc. Natl. Acad. Sci., USA., 91, 664–668)) or a sequence that is derived from the Drosophila melanogaster antennapedia protein. The latter is a peptide containing 16 amino acid residues taken from the third helix of the antennapedia homeodomain protein which translocates across biological membranes (Derossi et al (1994) J. Biol. Chem. 269: 10444–10450). This translocation peptide has the sequence: Arg-Gln-Ile-Lys-Ile-Trp-Phe-Gln-Asn-Arg-Arg-Met-Lys-Trp-Lys-Lys (SEQ ID NO:10). The peptide is preferably joined to the N-terminus of polypeptides of the invention which antagonize the interaction of VHL with an HIF α subunit.

Other candidate inhibitor compounds may be based on modelling the 3-dimensional structure of VHL and HIF α subunit and using rational drug design to provide potential inhibitor compounds with particular molecular shape, size and charge characteristics.

Assays of the invention and modulator compounds of the invention have a variety of uses. For example, the task of dissecting the complex pathways of cellular proliferation will facilitated by the provision of means to promote or inhibit a specific interaction, allowing the effects of other proteins in the pathway to be studied in better detail. Further, a means to promote angiogenesis by inhibiting the VHL-HIF interaction will allow compounds with anti-angiogenic potential to be evaluated in more detail. Such an evaluation may include providing an animal (particularly a small mammal like a mouse or rat) carrying a human xenograft, treating the xenograft in the animal with a modulator of the VHL-HIF interaction to promote angiogenesis, and then treating the xenograft with a compound with anti-angiogenic potential in conjunction with suitable controls.

Candidate modulator compounds obtained according to the method of the invention may be prepared as a pharmaceutical preparation.

Such preparations will comprise the compound together with suitable carriers, diluents and excipients. Such formulations form a further aspect of the present invention.

Formulations may be prepared suitable for any desired route of administration, including oral, buccal, topical, intramuscular, intravenous, subcutaneous and the like.

Formulations for topical administration to the skin may include ingredients which enhance the permeability of the skin to the peptides. Such formulations may be in the form of ointments, creams, transdermal patches and the like.

Formulations for administration by injection (i.m., i.v., subcutaneous and the like) will include sterile carriers such as physiological saline, optionally together with agents which preserve or stabilise the peptide. Albumin may be a suitable agent.

Formulations of inhibitor compounds in particular may be used in methods of treatment ischaemic conditions, such as organ ischaemia, such as is manifest in coronary, cerebrovascular and peripheral vascular insufficiency. Any ischaemia is a therapeutic target. The therapy may be applied in two ways; following declared tissue damage, e.g. myocardial infarction (in order to limit tissue damage), or prophylactically to prevent ischaemia, e.g. promotion of coronary collaterals in the treatment of angina. Additionally, vasomotor control is subject to regulation by HIF. Activation of HIF might lower systemic vascular resistance and hence systemic blood pressure.

Candidate inhibitor compounds may also be used in combination with promoters of angiogenesis. These include vascular endothelial growth factor and other angiogenic growth factors such as basic fibroblast growth factors and thymidine phosphorylase and pro-angiogenic and might be used in combination therapy. Other compounds which might conceivably be used in combination are 2-deoxy ribose and prostaglandin E.

In administering peptides of the invention to a subject, the doses will be determined at the discretion of the physician, taking into account the needs of the patient and condition to be treated. Generally, doses will be provided to achieve concentrations at a desired site of action that are from 0.1 $\mu$M to 1 mM, for example in the 1–10 $\mu$M range.

Peptides of the invention may be produced by standard recombinant means, or synthesised by chemical means, as described above. Thus in a further embodiment, the invention provides an expression vector comprising a promoter operably linked to a sequence encoding a peptide of the invention. The sequence may be linked to further sequences, for example leader sequences which direct the expression of the peptide to a cellular compartment or out of the cell. Vectors may be prokaryotic or eukaryotic. The vectors may include standard vector components such as an origin of replication, a selectable marker and the like.

The vector may be a viral vector such as an adenoviral or adeno-associated viral vector or the like suitable for expression of a peptide of the invention in human cells, including in methods wherein the vector is delivered to a cell such that expression of the polypeptide may occur. It is known that muscle cells are capable of taking up DNA administered directly to the cell, and in one embodiment the vector of the invention (particularly the abovementioned viral vectors) comprises a promoter which is operable in muscle cells, including muscle-specific promoters, and promoters inducible in muscle cells such as IGF-1 promoters.

The invention also provides host cells which carry a vector of the invention, methods of producing polypeptides of the invention by culturing the host cells under conditions to bring about expression from the vector, and desirably recovering the polypeptide.

The following examples illustrate the invention.

EXAMPLES

Hypoxia inducible factor-1 (HIF-1) plays a key role in a wide variety of cellular responses to hypoxia, including the regulation of genes involved in energy metabolism, vasomotor control, angiogenesis, proliferation and apoptosis (Wang, G. L., et al. Proc. Natl. Acad. Sci. USA 92, 5510–5514 (1995); Bunn and Poyton, Physiol. Rev. 76, 839–885 (1996); Carmeliet, P., et al. Nature 394, 485–490 (1998); An, W. G., et al. Nature 392, 405–408 (1998)). A major regulatory mechanism involves proteolysis of HIF α subunits which are rapidly degraded by the proteasome in normoxia but stabilised by hypoxia (Huang, L. E., et al. Proc. Natl. Acad. Sci. USA 95, 7987–7992 (1998)). Cobaltous ions or iron chelators mimic hypoxia—findings which have suggested that the stimuli interact through effects on a ferro-protein oxygen sensor (Goldberg, M. A., et al. Science 242, 1412–1415 (1988); Wang and Semenza, Blood 82, 3610–3615 (1993)). The present examples demonstrate a critical role for the von Hippel-Lindau tumour suppressor gene product pVHL in the regulation of HIF-1. In VHL defective cells HIF α subunits were constitutively stabilised and HIF-1 was activated. Transfection of a wild type VHL gene restored the oxygen dependent instability.pVHL and HIF α subunits co-immunoprecipitated, and pVHL was present in the hypoxic HIF-1 DNA binding complex. However, in cells exposed to iron chelation or cobaltous ions, HIF-1 was dissociated from pVHL. These findings suggest that the interaction between HIF-1 and pVHL is iron dependent and is necessary for the oxygen dependent degradation of HIF α subunits. They define a key function for pVHL in oxygen regulated gene expression and suggest that constitutive HIF-1 activation underlies the angiogenic phenotype of VHL associated tumours. The pVHL/HIF-1 interaction provides a new focus for understanding cellular oxygen sensing systems.

(a) Effect of pVHL on oxygen regulated gene expression in RCC4 cells.

Enhanced glucose metabolism and angiogenesis are classical features of cancer (Warburg, O. The metabolism of tumours (Arnold Constable, London, 1930); Hanahan and Folkman, Cell 86, 353–364 (1996)) involving upregulation of genes which are normally inducible by hypoxia. In addition to stimulation by the hypoxic microenvironment (Shweiki, D., et al. Nature 359, 843–845 (1992)), genetic alterations contribute to these effects. A striking example is von Hippel-Lindau (VHL) disease, a hereditary human cancer syndrome predisposing to highly angiogenic tumours (Kaelin and Maher, Trends Genet. 14, 423–426 (1998)). Constitutive up-regulation of hypoxically inducible mRNAs encoding VEGF and GLUT-1 in these tumour cells is correctable by re-expression of pVHL. A post-transcriptional mechanism has been proposed (Gnarra, J. R., et al. Proc. Natl. Acad. Sci. USA 93, 10589–10594 (1996); Iliopoulos, O., et al. Proc. Natl. Acad. Sci. USA 93, 10595–10599 (1996)). We studied the involvement of pVHL in oxygen regulated gene expression using ribonuclease protection analysis of two VHL deficient renal carcinoma lines, RCC4 and 786-O cells.

Eleven genes encoding products involved in glucose transport, glycolysis, high energy phosphate metabolism and angiogenesis were examined, nine of which are commonly induced by hypoxia in other mammalian cells and two of which (LDH-B and PFK-M) are repressed by hypoxia. Details of the genes and probes are in Table 1.

TABLE 1

Length and sequence of riboprobe templates.

| Probe | According. no. | 5' end | 3' end | Protected length | Total RNA hybridised (μg) |
|---|---|---|---|---|---|
| VEGF | M63971 | 2280 | 2502 | 140 | 30 |
| GLUT-1 | K03195 | 1063 | 1198 | 136 | 30 |
| AK-3 | X60673 | 563 | 761 | 199 | 30 |
| TGF-β1 | X02812 | 1204 | 1473 | 270 | 80 |
| ALD-A | M11560 | 609 | 738 | 130 | 10 |
| PGK-1 | M11960 | 9 | 197 | 121 | 10 |
| PFK-L | X15573 | 362 | 518 | 157 | 60 |
| PFK-C | D25328 | 752 | 918 | 167 | 60 |
| LDH-A | X02152 | 275 | 367 | 93 | 80 |
| PFK-M | M26066 | 251 | 363 | 113 | 100 |
| LDH-B | Y00711 | 225 | 348 | 123 | 8 |
| NRF-1 | L22454 | 803 | 955 | 153 | 60 |
| U6 snRNA | X01366 | 1 | 107 | 107 | 1 |
| β-Actin. | Y00474 | 1541 | — | 77 | 3 |
|  | M10277 | — | 348 |  |  |

Legend: VEGF, vascular endothelial growth factor; GLUT-1, glucose transporter 1; AK-3, adenylate kinase 3; TGF-b1, transforming growth factor-b 1; ALD-A, aldolase A; PGK-1, phosphoglyceratekinase 1; PFK, phosphofructokinase; LDH, lactate dehydrogenase; U6 sn, U6 small nuclear RNA; NRF-1 nuclear respiratory factor 1. U6 snRNA was used as an internal control in all assays. Also used were two other genes, NRF-1 and β-actin, which were not influenced by VHL status or hypoxia.

The U6 snRNA probe was synthesised in the presence of excess unlabelled GTP to yield a low specific activity probe. In each assay a 1 μg aliquot of RNA from each sample was hybridised to this probe, and after ribonuclease digestion a suitable proportion (corresponding to 10 to 45 ng of the original RNA) of this control hybridisation was added to the test hybridisation. ALD-A and PGK-1, and LDH-A and LDH-B could be hybridised together.

None of these responses were observed in the VHL defective cell lines. Responses to hypoxia were restored by stable transfection of a wild type VHL gene, effects ranging from a rather modest action of hypoxia (PFK-L and LDH-B) to substantial regulation. These results were observed in RCC4 cells, and similar, but in general smaller effects, were seen in 786-O cells. These results indicate that the previously described upregulation of hypoxia inducible mRNAs in VHL defective cells extends to a broad range of oxygen regulated genes and that it involves a constitutive 'hypoxia pattern' for both positively and negatively regulated genes.

(b) Effect of pVHL on HIF-1 and hypoxia response element (HRE) activity.

Since a number of these genes (VEGF, GLUT-1, AK-3, ALD-A, PGK-1, PFK-L, LDH-A) contain hypoxia response elements (HRE's) which bind the HIF-1 complex, and/or show altered expression in cells lacking HIF-1(Bunn and Poyton, Physiol. Rev. 76, 839–885 (1996); Dang and Semenza, Trends Biol. Sci. 24, 68–72 (1999) and references therein), this survey of expression in VHL defective cells prompted us to look for effects of pVHL on HIF-1 and HRE function under normoxic and hypoxic conditions. Transient transfections of RCC4 cells were performed with the VHL expression vector, pcDNA3-VHL (+), or empty vector pcDNA3 (-) and luciferase reporter genes containing no HRE, an HRE from the phosphoglycerate kinase-1 gene (PGK-1) or an HRE from the erythropoietin gene (Epo) linked to either the simian virus 40 (SV40) promoter or the thymidine kinase (TK) promoter.

VHL was found to markedly suppressed HRE activity in normoxic cells and restored induction by hypoxia (0.1% $O_2$, 24 hours). Similar results were obtained with exposure to 1% oxygen. Similar results were also obtained by sequential stable transfection of RCC4 cells with an HRE reporter plasmid then pcDNA3-VHL.

HIF-1 itself was examined by EMSA analysis using the Epo HRE. In a HeLa cell nuclear extract, the inducible HIF-1 species was seen as a doublet of a slower and faster mobility band. In RCC4 cells, only the faster mobility HIF-1 species is present, and is expressed at equivalent levels in both normoxia and hypoxia. In RCC4/VHL cells the HIF-1 binding pattern was similar to that in HeLa extracts, with restoration of the normal hypoxia inducible pattern in these RCC4 cells stably transfected with pcDNA3-VHL (RCC4/VHL). Constitutive binding species were also observed in all extracts.

In other cells, HIF-1 activation by hypoxia involves a major increase in HIF-1α abundance from low basal levels in normoxia (Wang, G. L., et al. Proc. Natl. Acad. Sci. USA 92, 5510–5514 (1995); Huang, L. E., et al. J. Biol. Chem. 271, 32253–32259 (1996)). Western blotting of whole cell extracts showed that RCC4 cells express constitutively high levels of both HIF-1α itself and a related molecule, HIF-2α (also termed EPAS-1, HRF, HLF, and MOP2) which is normally regulated in a similar way (Wiesener, M. S., et al. Blood 92, 2260–2268 (1998)).

Constitutively high levels of these proteins were found in eight other VHL deficient cell lines (see list in Table 2 below) by Western analysis of whole cell extracts for HIF-1α and HIF-2α. UMRC2, UMRC3 and KTCL140 are renal carcinoma lines with mutations in VHL (Gnarra, J. R., et al. Nature Genet. 7, 85–90 (1994)). The cell lines with VHL mutations showed high normoxic levels of HIF α subunits. This was in contrast to the renal carcinoma line Caki-1 (which expresses pVHL normally (Iliopoulos, O., et al. Nature Med. 1, 822–826 (1995))).

Certain VHL deficient cells (e.g. 766-O, KTCL140) expressed HIF-2α at a high constitutive level but did not express HIF-1α protein at a detectable level. Examination of stable transfectants of RCC4 and 786-O cells demonstrated that expression of wild type, but not a truncated, VHL gene restored regulation of HIF α subunits by oxygen without affecting the levels of mRNA encoding either subunit.

TABLE 2

HIF α subunit expression in renal carcinoma cells bearing VHL mutations.
The renal carcinoma cell lines detailed below showed high normoxic expression of HIF α subunits by Western analysis.

| Cell line | VHL mutation | Effect | HIF α subunit expression |
|---|---|---|---|
| A498 | 4 nt deletion 639–642 | FS codon 142 | HIF-2α, no HIF-1α |
| 786-O | 1nt deletion 523 | FS codon 104 | HIF-2α, no HIF-1α |
| RKF-393 | Methylation | Not expressed | HIF-2α, HIF-1α |
| RCC7 | 1bp insertion nt 746 | FS codon 178 | HIF-2α, no HIF-1α |
| RCC4 | C to G nt 407 | Ser to Trp codon 65* | HIF-2α, HIF-1α |
| UMRC2 | G to C nt 458 | Arg to Pro codon 82 | HIF-2α, HIF-1α |
| SKRC28 | C to A nt 470 | Pro to His codon 86 | HIF-2α, HIF-1α |
| UMRC3 | T to A nt 479 | Leu to His codon 89 | HIF-2α, HIF-1α |
| KTCL140 | C to T nt 556 | His to Tyr codon 115 | HIF-2α, no HIF-1α |

Legend: Mutations as reported (Gnarra, J. R., et al. Nature Genet. 7, 85–90 (1994)) or as determined by us (RCC4 and RCC7). *pVHL not detected on Western blot in RCC4 cells. The mutation did not affect recognition by IG32 (assessed by immunoblotting of wild type and mutant protein, expressed in COS cells and by IVTT).

(c) Association of pVHL with HIF-1.

To pursue the role of pVHL in HIF-1 regulation we tested for interactions between HIF α subunits and pVHL using a combination of hypoxia and/or proteasomal blockade to induce HIF α subunits. Immunoprecipitation of whole cell extracts from RCC4 cells stably transfected with pcDNA3-VHL (RCC4/VHL; VHL+), and RCC4 cells (VHL-) with anti-pVHL monoclonal antibody IG32 was performed.

Cells were cultured for 4 hours in normoxia or hypoxia (1% $O_2$, 4 hours) with or without proteasomal inhibition. Cell lysates were immunoprecipitated with IG32 or control antibody (VG-7be) and immunoblotted for HIF-2α (using 190b) and HIF-1α (clone 54). Aliquots of selected input lysates (15 μg, equivalent to ¼ of that analysed by immunoprecipitation for each a subunit) were also loaded on the gels.

It was found that anti-pVHL immunoprecipitates of extracts from proteasomally blocked RCC4/VHL cells, but not RCC4 cells, contained both HIF-1α and HIF-2α.

Similar results were obtained with hypoxia in the absence of proteasomal blockade. The inverse reactions were also performed, that is immunoprecipitation of RCC4/VHL (VHL+) and RCC4 (VHL-) extracts with polyclonal antibodies to HIF α subunits. Cell lysates were immunoprecipitated using rabbit polyclonal Ig to HIF-2α (HIF-2α), HIF-1α (HIF-1α) or normal rabbit Ig and immunoblotted for pVHL (IG32). Immunoprecipitating antibodies to HIF-2α or HIF-1α co-precipitated pVHL, although a smaller proportion of the total was captured.

The interaction was also demonstrated by the presence of HIF α subunits in anti-pVHL immunoprecipitates of HeLa cells which express pVHL normally. Immunoprecipitation of Hela extracts with IG32 or pAb419 followed by immunoblotting for HIF 2-α (190b) and HIF-1α (affinity purified rabbit polyclonal) was performed, with 30 μg of the input lysates was also loaded on the gels, and the interaction was observed.

Since a proportion of pVHL localises to the nucleus we next determined whether pVHL is incorporated in the HIF-1

DNA binding complex. Anti VHL (IG32), or VG-7be (control), was added to binding reactions of nuclear extracts from normoxic or hypoxic (1% $O_2$, 4 hours) cells. Control antibody did not alter the mobility of either the slower or faster mobility HIF-1 species. Anti-pVHL antibody supershifted the slower HIF-1 species in HeLa and hypoxic RCC4/VHL cells. No supershift was seen with extracts of hypoxic RCC4 cells, which lack pVHL and the slower HIF-1 species. Thus addition of anti-pVHL to nuclear extract from RCC4/VHL cells and HeLa cells produced a clear change in mobility, whereas no such mobility shift was observed with nuclear extract from VHL defective RCC4 cells.

The gels resolved HIF-1 into two species. Only the slower mobility HIF-1 species was shifted by anti-pVHL in nuclear extracts from hypoxic HeLa cells, whereas both species were shifted by antibodies against HIF-1α. Similar results were obtained in other cell lines (Hep3B, Caki-1, MRC5-V2 and 293 cells).

Furthermore, whereas RCC4/VHL, HeLa cells and other cell lines clearly contained the two HIF-1 species, both normoxic and hypoxic RCC4 extracts contained only the faster mobility species. Thus, VHL defective cells lack the slower mobility species which is restored by transfection of wild type VHL, and shifted by anti-pVHL. This indicates that the HIF-1 doublet apparent in EMSA analysis arises from two species of the HIF-1 complex, containing or not containing pVHL. Combination supershift analysis confirmed that the slower mobility species contained both HIF-1α and pVHL.

(d) Effect of cobaltous ions and iron chelation on the pVHL/HIF-1 interaction.

HIF-1 activation by hypoxia is mimicked by cobaltous ions and iron chelation (Goldberg, M. A., et al. Science 242, 1412–1415 (1988); Wang and Semenza, Blood 82, 3610–3615 (1993)). To pursue the mechanism of VHL action we tested whether the pVHL/HIF-1 interaction was regulated by any or all of these stimuli. Proteasomal blockade induces a HIF-1 DNA binding complex in normoxic cells (Salceda and Caro, J. Biol. Chem. 272, 22642–22647 (1997)); comparison of this normoxic complex with EMSA of hypoxic cells in the presence or absence of proteasomal inhibitors showed a similar shift and anti-pVHL supershift. RCC4/VHL cells were cultured for four hours in normoxia, hypoxia (1% $O_2$), desferrioxamine (100 $\mu$M), cobaltous chloride (100 $\mu$M) or proteasomal inhibition (PI). Together with immunoprecipitation data this suggests that the interaction with pVHL occurs in normoxia and hypoxia, and in the presence or absence of proteasomal inhibition. In contrast EMSA analysis of RCC4/VHL cells treated with cobalt and the iron chelator desferrioxamine (DFO) demonstrated only the faster mobility HIF-1 complex. This did not supershift with anti-pVHL, suggesting that the lower mobility pVHL/HIF-1 complex could not form in cells exposed to these stimuli. Similar results were obtained in other cell types and are consistent with hitherto unexplained mobility differences in previous analyses of HIF-1 from cobalt or DFO versus hypoxia stimulated cells (Wang and Semenza, Blood 82, 3610–3615. (1993))—indicating that this is a general effect.

Treatment with DFO four hours prior to hypoxia prevented the pVHL/HIF-1 complex forming. Addition of iron chelators was not able to break the pVHL/HIF-1 complex in vitro, whereas addition of in vitro translated wild type pVHL (but nota truncated pVHL) could restore the slower mobility species to nuclear extracts of proteasomally blocked normoxic, and hypoxic RCC4 cells, but not DFO or cobalt treated cells.

Immunoprecipitation studies were consistent with the EMSA analysis in indicating that the interaction between HIF-1 and pVHL is iron dependent. Whereas both HIF-1α and HIF-2α were contained in immunoprecipitates from hypoxic RCC4/VHL cells neither protein was contained in similar precipitates from DFO or cobalt treated cells. The iron-dependent interaction between HIF α subunits and pVHL may be direct or indirect. To examine this, the effect of adding IVTT pVHL to a native HIF-1 complex compared to an in vitro transcribed translated HIF-1 complex was examined. EMSA was performed with nuclear extract from hypoxic RCC4 cells or IVTT HIF-1α and ARNT. Antibody to HIF-1α supershifted the HIF-1 complex. Addition of IVTT pVHL modified the RCC4 HIF-1 complex, resulting in a doublet which included the slower mobility HIF-1 species which was supershifted by IG32. Addition of IVTT pVHL did not modify the IVTT HIF-1 complex. Thus, in vitro translated wild type pVHL did not bind to an in vitro translated HIF-1 DNA binding complex, in contrast to the interaction with RCC4 extracts, suggesting that an additional factor or modification of HIF-1 not represented in rabbit reticulocyte lysates is necessary for the association.

(e) Effect of pVHL on HIF α stability and function of the oxygen dependent degradation (ODD) domain.

Normally HIF α subunits are targeted for rapid degradation in normoxic cells by a proteasomal mechanism operating on an internal oxygen dependent degradation (ODD) domain (Huang, L. E., et al. Proc. Natl. Acad. Sci. USA 95, 7987–7992 (1998)). Our data suggest that pVHL might normally be required for this process—a possibility which would be consistent with recent data that pVHL forms a multiprotein complex (containing Cul-2 and elongins B and C) which has homology with ubiquitin ligase/proteasome targeting complexes in yeast (Pause, A., et al. Proc. Natl. Acad. Sci. USA 94, 2156–2161 (1997); Lonergan, K. M., et al. Mol. Cell Biol. 18, 732–741 (1998)). When cells were switched from hypoxia (4 hours) to normoxia with the addition of cycloheximide (final concentration 100 $\mu$M), HIF α subunits decayed with a half-life in the region of 5 minutes in wild type VHL transfectants, compared to ~60 minutes in the VHL defective RCC4 and 786-O cells confirming a major effect of pVHL on stability.

Moreover, functional studies of Gal4 chimeras containing the HIF-1α ODD domain demonstrated a striking dependence of the isolated ODD domain on pVHL. Hep3B cells or RCC4 cells were transfected with the Gal4 reporter pUAS-tk-Luc, and either pGalVP16 encoding a Gal4/VP16 fusion gene or pGala344-698VP16 encoding a similar fusion linking HIF-1α amino acids 344–698 (which includes the entire ODD domain (Huang, L. E., et al. Proc. Natl. Acad. Sci. USA 95, 7987–7992 (1998))) between the Gal4 DNA binding domain and the VP16 activation domain. RCC4 cells were co-transfected with pcDNA3, pcDNA3-VHL, or pcDNA3-VHL.103FS. After transfection, cells were divided for 24 hours incubation in normoxia, or hypoxia (0.1% $O_2$). Corrected luciferase counts were determined, normalised for each cell type to the value obtained with pGalVP16 or pGalVP16+pcDNA3 in normoxic cells. The HIF-1α sequence confers marked suppression and regulation by hypoxia in Hep3B cells but not RCC4 cells, where these properties are restored by co-transfection with wild type but not truncated VHL.

(f) Interaction between pVHL and HIF-1α sequence.

Reticulocyte lysates were programmed in the presence of $^{35}S$ methionine with vectors encoding HIF-1α subsequences (549–652 and 572–652) and with vectors encoding VHL cDNA and a VHL cDNA with a missense mutation changing codon 65 from Ser to Trp. In each experiment, a lysate containing HIF-1α sequence was mixed with a lysate containing a pVHL. Anti pVHL antibody was added, followed by protein G beads. Proteins were eluted, resolved by SDS-PAGE and visualised by fluorography. The 549–652 subfragment of HIF-1α interacted with wild type pVHL, but the smaller 572–652 fragment did not, defining a region from 549–572 which contains a region important for the interaction between the two proteins. The missense mutation of pVHL also abolished the interaction with the larger protein.

(g) Ubiquitylation assay.

To test the hypothesis that pVHL is a necessary component of a ubiquitin ligase complex recognising HIF-α we developed an in vitro ubiquitylation assay for HIF-1α. In this assay, cell extracts (initially from Cos-7) were incubated with [$^{35}$S]labelled HIF-1α prepared in vitro in reticulocyte lysates. This was used as substrate in reactions with different combinations of extract, an ATP-regenerating system, ubiquitin aldehyde, and methylated ubiquitin. Reactions were incubated at 30° C. for 270 minutes before analysis by SDS-PAGE.

Incubation with extract alone converted the HIF-1α substrate to a slower migrating form, an effect which was enhanced by an ATP-regenerating system, and was prevented by addition of the protein kinase inhibitor 2-aminopurine. This indicated that these mobility shifts were most likely due to phosphorylation of HIF-1α as demonstrated recently by others (Richard, D. E., et al, (1999) *J. Biol. Chem.* 274, 32631–32637). Addition of ubiquitin resulted in the conversion of these species to a high molecular weight [$^{35}$S]labelled protein ladder of polyubiquitylated HIF-1α species. This assignment was confirmed by enhancement with addition of ubiquitin aldehyde, an isopeptidase inhibitor that prevents the breakdown of ubiquitin conjugates. In contrast addition of methylated ubiquitin, which prevents the formation of multiubiquitin chains and acts as a chain terminator (Hershko, A., et al (1991) *J. Biol. Chem.* 266(25), 16376–9), did not support the generation of high molecular weight species, and when added in an equimolar ratio inhibited the formation of these species.

(h) Role of pVHL in HIF-1α ubiquitylation.

To determine the role of pVHL in HIF-1α ubiquitylation, we performed similar assays using extracts from RCC4 cells, and different stable transfectants re-expressing pVHL or pVHL.HA. [$^{35}$S] labelled HIF-1α was incubated at 30° C. in reactions consisting of cell extract, ATP-regenerating system, ubiquitin and ubiquitin aldehyde, for periods of 30, 90 and 270 minutes. Comparison of extracts from VHL defective, and pVHL re-expressing cells showed large differences in the rate of ubiquitylation of the HIF-1α substrate, particularly in the generation of the highest molecular weight conjugates, which accumulated in the re-expressing transfectants, whereas the phosphorylation of HIF-1α occurred at a similar rate. Similar effects were seen for HIF-2α.

We further determined quantitative results in four independent comparisons of pairs of extracts from different VHL defective and pVHL re-expressing RCC4 sublines. Though HIF-1α ubiquitylation was clearly more efficient in VHL competent cells, a low level was apparent in the defective cells.

(i) N-terminal truncated pVHL binds HIF-α.

As a first step towards understanding the precise requirements for capture and regulation of HIF-α destruction by pVHL we set out to determine the necessary pVHL sequences. To do this we constructed a series of stable transfectants of RCC4 cells expressing epitope tagged mutant pVHL molecules. This enabled differences in the capture of labelled protein species to be compared with functional effects on the regulation of HIF-α and hypoxia inducible gene expression. Preliminary experiments demonstrated that restoration of HIF-α regulation by wild type pVHL was similar in transfectants expressing pVHL at differing levels, and was unaffected by the presence of the HA epitope at either the N or the C-terminus of the molecule. A series of stable transfectants bearing different truncations of pVHL was metabolically labelled under conditions of proteasomal blockade. Analysis of N-terminal truncations indicated that whilst removal of codons 1–53 (which effectively creates the p19 species of pVHL resulting from translational initiation at codon 54) had no effect on capture of HIF-α, though further truncation to codon 72 almost completely abolished the capture. Analysis of C-terminal truncations demonstrated that truncation to codon 187 greatly reduced capture of HIF-2α, and abolished capture of HIF-1α, whilst truncation to codon 156 abolished capture of both species.

(j) Subsequences of the HIF-α subunits.

We next wished to define the subsequences of the HIF-α subunits that are recognised by pVHL. Since stable overexpression of transfected HIF-α subunits has presented substantial problems, we sought to define an in vitro system to enable further studies of the pVHL/HIF-α interaction.

In a cell free system using labelled proteins produced in rabbit reticulocyte lysates both HIF-1α and HIF-2α were found to interact with pVHL. Testing of N-terminal pVHL truncations in this assay demonstrated that whilst truncation to the second initiation site at codon 54 did not alter binding. We proceeded to examine series of fusion proteins containing full length or truncated HIFa subunits fused with either the glucocorticoid receptor or GAL4 DNA binding domains. These fusion proteins have previously been used to characterise regulatory and transactivation domains in HIF-1α and HIF-2α (Pugh, C. W. et al (1997) *J. Biol. Chem.* 272, 11205–11214; O'Rourke, J. F., et al (1999) *J. Biol. Chem.* 274, 2060–2071). In the first series of experiments we examined a series of truncations of HIF-1α (27–826, 166–826, 244–826, 329–826, 530–826, 652–826, 27–826, 27–652 and 27–329). Although there was some variation in the efficiency of capture among interacting molecules, we observed a: marked reduction in capture with the C-terminal truncations proximal to residue 652, and with the N-terminal truncations distal to reside 530.

Testing of a similar series of truncations of HIF-2α (19–870, 19–819, 19–682, 19–495, 19–416, 295–870, 345–870, 495–870, 517–870 and 742–870) showed a marked reduction in capture with the C-terminal truncations proximal to residue 682 and with the N-terminal truncations distal to residue 517. Taken together these findings implicate the HIF-1α sequences 530–652 and the HIF-2α sequences 517–682 in the pVHL interaction. For each molecule, these sequences correspond to an internal transactivation domain, which overlaps with the oxygen dependent degradation domain.

We next examined whether these transactivation domains were sufficient to interact with pVHL. We found that the sequences 530–634 of HIF-1α and 517–682 of HIF-2α are indeed sufficient for interaction with pVHL. To further investigate the interaction we tested deletions and subsequences within this domain and sought to correlate pVHL binding in vitro with our previous in vivo functional analyses of oxygen regulated activity. For, HIF-1α amino acid sequences 530–634, 549–634, but not 572–634 could be captured by pVHL whereas for HIF-2α, amino acids 517–682, but not 534–682 could be captured by pVHL. The data show exact concordance between competence for pVHL binding and the previously reported ability of these fusion proteins to convey oxygen regulated responses in transiently transfected Hep3B cells, and showed that HIF-1α residues 549–572 and HIF-2α residues 517–534 are critical for pVHL binding. Finally we tested previously defined minimal oxygen regulated domains for pVHL interaction and found that HIF-1α sequences 549–582, and the homologous HIF-2α sequences. 517–552 were sufficient for interaction with pVHL.

(k) Further definition of minimal HIF-1alpha sequence required to interact with pVHL in vitro.

Reticulocyte lystaes were programmed in the presence of $^{35}$S methionine with vectors encoding HIF-1 subsequences 556–574, 549–574, 556–582 and 549–582 (in the presence or absence of 100 μM Fe2+ and 100 μM Fe3+) and with vectors encoding VHL cDNA with a C-terminal haemagglutinin affinity tag. In each experiment lysate containing pVHL was mixed with lysate containing HIF-1 sequence. Anti haemagglutinin antibody was added followed by protein G beads. Proteins were eluted, resolved by SDS-PAGE and visualised by fluorography. It was observed that that pVHL interacted with each of the subsequences that contain codons 556–574. In all cases, it was found that the presence of iron ions caused a substantial increase in the amount of the interaction.

(1) Definition of residues critical for the interaction.

Reticulocyte lystaes were programmed in the presence of $^{35}$S methionine and 100 μM iron with vectors encoding the HIF-1 subsequence 549–582, and missense mutations F572A, P564G, D569N, DDD569–571NNN, D556N, E560Q P567R, M568R and Y565Q, and with vectors encoding VHL CDNA with a C-terminal haemagglutinin affinity tag. In each experiment lysate containing pVHL was mixed with lysate containing HIF-1 sequence or one of the mutated versions. Anti haemagglutinin antibody was added followed by protein G beads. Proteins were eluted, resolved by SDS-PAGE and visualised by fluorography. This confirmed that pVHL interacts with the wild type sequence 549–582, and it was further observed that the single mutations at residues 564, 565, 567, 568 and of the three residues 569–572 abolish the interaction. The changes at 569, 556, 558 and 560 did not have an effect in this experiment.

(m) HIF-1alpha can be modified to enhance or diminish the interaction.

Reticulocyte lystaes were programmed in the presence of $^{35}$S methionine with a vector encoding HIF-1α under normal conditions, or in the presence of 100 μM Fe2+ and 100 μM Fe3+, or in the presence of 100 μM cobaltous ions, or in the presence of 100 μM nickel ions. Reticulocyte lysate was also programmed with VHL cDNA with a C-terminal haemagglutinin affinity tag. In each experiment lysate containing pVHL was mixed with lysate containing HIF-1α. Anti haemagglutinin antibody was added followed by protein G beads. Proteins were eluted, resolved by SDS-PAGE and visualised by fluorography. As indicated above, it was found that translating HIF-1α in the presence of iron enhances the interaction with pVHL. It was also observed that translation in the presence of cobaltous irons or nickel diminishes it.

(n) Inhibition of HIFα-VHL interaction with a synthetic peptide.

A. Interaction of proteins in reticulocyte lysates was studied essentially as above. A synthetic peptide consisting of amino acids 549–582 (SEQ ID NO:9) (final concentration 1 μg/ml of the peptide) was mixed with the haemagglutinin tagged pVHL containing lysate prior to addition of lysate containing labelled HIF-1α. Anti-HA retrieval of HIF-1 was not influenced by the peptide.

B. A synthetic peptide consisting of amino acids 549–582 was first incubated with reticulocyte lysate. This peptide-containing lysate, or an equivalent amount of control lysate was mixed with lysate containing $^{35}$S labelled haemagglutinin tagged pVHL prior to addition of lysate containing labelled HIF-1α. Anti-HA retrieval of HIF-1α was prevented by prior incubation of the pVHL with the lysate-treated peptide. These experiments (a) show that reticulocyte lysate can make an important modification to the HIF-1α subsequence, influencing its ability to prevent the pVHL-HIF modification, supporting the principle of assays for HIF modifying activities and (b) demonstrate that a peptide of 33 amino acids can interfere with the pVHL-HIF interaction.

(o) Ubiquitylation as a read out for the HIFalpha-pVHL interaction.

An experiment similar to that of section (h) above was performed but with the ommission of ubiquitin aldehyde pVHL was generated by in vitro transcription translation, and HIF-1α was also generated in reticulocyte lysate in the presence or absence of 100 μM Fe2+ and Fe3+. Enhanced ubiquitylation (as evidenced by the appearance of high molecular weight species) and destruction (as evidenced by more rapid disappearance of the HIF-1α) was observed when the HIF-1α was produced in the presence of the iron ions Thus assays of the invention may be used for the identification of compounds acting at a point distal to the HIF-pVHL interaction (i.e. not altering binding but interfering with tagging or destruction). It also provides further evidence for modifications of HIF influencing its ability to bind pVHL. Accordingly, the invention provides an assay for a modulator which influences, though particularly promotes, VHL-HIF α subunit interaction, which assay comprises:

a) bringing into contact a HIF α subunit protein and a putative modulator compound in the presence or absence of a VHL protein, b) providing a VHL protein where said protein is absent in step (a); and c) determining whether the VHL-HIF α subunit interaction has been influenced by the presence of the modulator.

As with other embodiments of the invention, the HIF α may be produced in a recombinant, cell-free system, or in a native environment in cell (e.g. a human or mammalian cell, such as in cell culture) and the effect of the modulator on the ability of HIF α to interact with VHL is determined either by providing the putative modulator during production of the HIF α subunit, incubating the subunit with the putative modulator prior to contact with VHL, or in the presence of VHL. The effect determined may be either an increase or decrease in affinity. Modulators which provide an increase in affinity will be useful to enhance or promote cell death, or to interfere with the process of angiogenesis. Thus such modulators will be useful in controlling cell proliferation in disease states such as cancer, pre-cancerous cell growth, psoriasis, etc. Compounds obtainable by such an assay form a further aspect of the invention.

Methods

Cells and transfections.

786-O cells expressing full length pVHL, truncated pVHL (amino acids 1–115), or transfected with empty vector (Iliopoulos, O., et al. Nature Med. 1, 822–826 (1995)) were a gift from W. G. Kaelin. RCC4 cells were a gift from C.H.C.M. Buys. Other RCC lines were provided by M. Lerman. HeLa and Hep3B cells were from ECACC. RCC4 cells and Cos7 cells were maintained in DMEM with 10% foetal calf serum. RCC4/VHL was obtained by transfecting with pcDNA3-VHL followed by G418 selection. Cells were subdivided into medium lacking G418 for parallel incubation 24 hours before experiments, which were generally performed using cells approaching confluence in 75 cm$^2$ dishes. Proteasomal inhibition was with 100 $\mu$M Calpain inhibitor I and 10 $\mu$M N-carbobenzoxyl-L-leucinyl-L-leucinyl-L-norvalinal. Transient transfections were performed by electroporation. Aliquots of transfected cells were split for parallel normoxic and hypoxic incubation (Napco 7001, Precision Scientific). Firefly luciferase reporter gene activities were measured using a commercial assay (Promega) and corrected for transfection efficiency by assay of $\beta$-galactosidase expression from the co-transfected control plasmid pCMV-$\beta$Gal. Hypoxic incubation, unless stated otherwise, was in an atmosphere of 1% oxygen/5% $CO_2$/balance nitrogen in a Napco 7001 incubator (Jouan). For radio-isotopic labelling, cells were first incubated for one hour in serum-free medium lacking methionine and cystine, which was replaced with 4.5 ml medium lacking methionine and cystine with 2% dialysed foetal calf serum and 200 $\mu$Ci/ml [$^{35}$S]methionine/cystetine (Pro-mix, Amersham Pharmacia).

RNA analysis.

Total RNA was extracted with RNAzolB (Biogenesis) and aliquots hybridised to $^{32}$P antisense riboprobes for analysis by ribonuclease protection. Riboprobes were synthesised using SP6 or T$^7$ polymerase (probe details are given in Table S1). Assays were controlled internally by hybridisation with a probe for U6 small nuclear RNA.

Plasmid constructions.

pcDNA3-VHL contained nucleotides 214 to 855 of Genbank accession no. L15409, encoding full length pVHL, in pcDNA3 (Invitrogen). pcDNA3-VHL.103FS was made using site directed mutagenesis to delete nucleotides 522–523, resulting in a frameshift at codon 103. To make pcDNA3-VHL.HA, pcDNA3-VHL was PCR amplified with primers 5'-AGGGACACACGATGGGCTTCTG-3' (SEQ ID NO:11) and: 5'-gcagaattcggcttcacaagctagcgtaatctggaacatcgtatgggtatcca tctcccatccgttgatgtggc-3' (SEQ ID NO:12). The PCR product was cut at an internal BglII site and at the EcoRI site incorporated into the 3' oligonucleotide, and used to replace a corresponding fragment in pcDNA3-VHL. pcDNA3-HA.VHL contained the sequence encoding pVHL with an HA epitope tag at the N terminus from pRC-HAVHL (a gift from W. Kaelin) inserted as a HindIII-XbaI restriction fragment into pcDNA3.1. pcDNA3(54–213).HA was derived from pcDNA3-VHL.HA by removal of a HindIII-HaeII restriction fragment, followed by repair with DNA polymerase I Klenow fragment and religation. HRE reporter genes were based on pGL3-basic (Promega) or pPUR (Clontech) and contained either a minimal SV40 promoter or a minimal (−40 bp) thymidine kinase promoter linked to a firefly luciferase gene. The hypoxic response element plasmids contained multimerized HRE as follows:

PGK-1 HRE, 5'-CGCGTCGTGCAGGACGTGACAAAT-3' (SEQ. ID NO:13) sense strand from the 5'enhancer-promoter region of the murine gene Epo HRE, 5'-GCCCTACGTGCTGCCTCGCATGGC-3' (SEQ ID NO:14) sense strand from the 3' enhancer of the murine gene.

The Gal4 fusion plasmids were based on pcDNA3 (Invitrogen). pGalVP16 encoded the Gal4 DNA binding domain (amino acids 1–147) linked in frame to the activation domain (amino acids 410–490) from herpes simplex virus protein 16; pGala344-698VP16 encoded the indicated amino acids of HIF-1$\alpha$ between those domains. Plasmid pUAS-tk-Luc contained two copies Of the Gal4 binding site linked to a thymidine kinase promoted luciferase reporter gene. The plasmids encoding different series of GAL4 fusions with HIF-1$\alpha$ (pGal/$\alpha$/ARNT-ta) and HIF-2$\alpha$ (pGal/EPAS), and glucocorticoid receptor fusions with HIF-1$\alpha$ (pGR/a) have been described previously (Pugh, C. W., et al (1997) J. Biol. Chem. 272, 11205–11214; O'Rourke, J. F. et al, (1999) J. Biol. Chem. 274, 2060–2071). Plasmids based on pcDNA3 expressing the entire ORFs of human HIF-1$\alpha$, human HIF-2$\alpha$, human HIF-1$\beta$, rat IRP-2 and human c-Myc were made by standard recombinant manoeuvres.

Antibodies.

Anti-HA antibody (12CA5) was from Roche, anti-pVHL antibody (IG32) was from Pharmingen, anti-HIF-1$\alpha$ antibody (clone 54) was from Transduction Laboratories, polyclonal anti-GLUT1 antibody (GT-11A) was from Alpha Diagnostic and antibody to SV40 T antigen (PAb419) was a gift from E. Harlow. Anti-HIF-2$\alpha$ antibody (190b) was described previously (Wiesener, M. S., et al (1998) Blood 92, 2260–2268).

Cell lysis, immunoblotting and immunoprecipitation.

Whole cell extracts were prepared by homogenisation in denaturing conditions and aliquots immunoblotted for HIF $\alpha$ subunits with 28b (anti-HIF-1$\alpha$), and 190b, or using clone 54. For immunoprecipitation, lysis was performed in 100 mM NaCl, 0.5% Igepal CA630, 20 mM Tris-HCl (pH7.6), 5 $\mu$M $MgCl_2$, 1 mM sodium orthovanadate with aprotinin (10 $\mu$g/ml), "Complete" protease inhibitor (Boehringer) and 0.5 mM 4-(2-aminoethyl)benzene sulphonyl fluoride for 30 minutes to one hour on ice. After clearance by centrifugation, in examples (a) to (f) 120 $\mu$g aliquots of cell lysate were incubated for 2 hours at 4° C. with 4 $\mu$g affinity purified anti-HIF-2$\alpha$ polyclonal antibodies (raised against a bacterially expressed fusion protein including amino acids 535–631) or 4 $\mu$g ammonium sulphate precipitated anti-HIF-1$\alpha$ polyclonal antibodies (raised against a bacterially expressed fusion protein including amino acids 530–652) in parallel with normal rabbit immunoglobulin (control), or alternatively with 0.7 $\mu$g anti-pVHL antibody (IG32, Pharmingen) or control (antibody to SV40 T antigen, pAb419, a gift from E. Harlow or antibody to VEGF, VG-7be, a gift from H. Turley). 10 $\mu$l conjugated agarose beads pre-blocked with 20 mg/ml BSA was added and lysates incubated for a further 2 hours with rocking. Pellets were washed five times and eluted with sample buffer. Eluates were divided into aliquots for immunoblot analysis. A similar protocol was used where applicable in sections (g) to (o). Briefly, following centrifugation, 200 $\mu$g of cell extract was pre-cleared overnight at 4° C. with 10 $\mu$l of protein G sepharose beads pre-blocked with phosphate buffered saline containing 20 mg/ml bovine serum albumin. 1 $\mu$g antibody was then added and samples incubated at 4° C. for two hours, followed by two hours incubation with 10 $\mu$l pre-blocked protein G sepharose beads on a rotator. Beads were washed five times in lysis buffer. Samples were resolved by SDS-PAGE, generally using discontinuous gels (8% acylamide upper portion, 13% lower portion) and were detected by fluorography (Amplify, Amersham Pharmacia).

Electrophoretic mobility shift and supershift assays.

Nuclear extracts were prepared using a modified Dignam protocol and 5 µg (HeLa) or 7.5 µg (RCC4) incubated with a $^{32}$P labelled 24 bp oligonucleotide probe (sense strand; 5-GCCCTACGTGCTGCCTCGCATGGC-3' (SEQ ID NO:15)) from the mouse Epo 3' enhancer as described (Wood, S. M., et al. J. Biol. Chem. 273, 8360–8369 (1998)). For supershift assays, 0.5 µg IG32, VG-7be (isotype and subclass matched control for IG32) or clone 54 (anti-HIF-1α) was added and reactions were incubated for 4 hours at 4° C. prior to electrophoresis. In vitro transcription translations of pcDNA3-VHL and pcDNA3-VHL.103FS were performed using reticulocyte lysate (Promega); 2 µl of a 1:10 dilution in PBS was added to binding reactions 2 hours prior to electrophoresis or addition of antibody.

In vitro translation.

[$^{35}$S]methionine-labelled proteins were prepared by coupled transcription and translation reactions of expression plasmids in rabbit reticulocyte lysate (TNT, Promega).

In vitro interaction assay.

[$^{35}$S]methionine-labelled proteins were produced in reticulocyte lysates programmed with plasmids encoding HA epitope tagged pVHL and HIF-α sequences. 1 µl of the indicated lysates was mixed in 100 µl NETN buffer (150 mM NaCl, 0.5 mM EDTA, 20 mM Tris-HCl pH8.0, 0.5% v/v Igepal CA630). After 90 minutes at 4° C., 0.25 µg anti-HA antibody was added, followed after a further 1 hour by 10 µl pre-blocked protein G sepharose beads. After 30 minutes mixing on a rotator, beads were washed three times with NETN buffer. Proteins were analysed by SDS-PAGE followed by fluorography.

In vitro ubiquitylation assay. To prepare extracts cells were washed twice with cold hypotonic extraction buffer (20 mM Tris pH7.5, 5 mM KCl, 1.5 mM MgCl$_2$, 1 mM dithiothreitol). After removal of buffer, cells were disrupted in a Dounce homogeniser. Following lysis, crude extract was centrifuged at 10,000×g for 10 min at 4$_i$ C. to remove cell debris and nuclei, and stored in aliquots at −70$_i$C. Ubiquitylation assays were carried out at 30$_i$C in a total volume of 40 µl, containing 2 µl programmed reticulocyte lysate, 27 µcell extract, 4 µl 10×ATP-regenerating system (20 mM Tris, pH7.5, 10 mM ATP, 10 mM magnesium acetate, 300 mM creatine phosphate, 0.5 mg/ml creatine phosphokinase), 4 µl 5 mg/ml ubiquitin (Sigma) or methylated ubiquitin (AFFINITI Research Products), 0.83 µl 150 µM ubiquitin aldehyde (AFFINITI Research Products). For pVHL reconstitution experiments, [$^{35}$S]methionine-labelled wild-type or mutant pVHL (4 µl programmed reticulocyte lysate) was pre-incubated with the reaction mixture at room temperature for 5 min prior to addition of substrate. Aliquots were removed at indicated times, mixed with SDS sample buffer and analysed by SDS-PAGE and autoradiography. Gels were quantitated using a Storm 840 PhosphorImager (Molecular Dynamics).

All publications, patent applications and sequence accession disclosures cited in this specification are herein incorporated by reference as if each individual publication, patent application or sequence were specifically and individually indicated to be incorporated by reference.

Although the foregoing invention has been described in some detail by way of illustration and example for the purposes of clarity and understanding, it will be readily apparent to those of skill in the art that certain changes and modifications may be made thereto without departing from the spirit or scope of the appended claims.

What is claimed is:

1. An assay for a modulator of VHL-HIF α subunit interaction, which comprises:
   a) bringing into contact a VHL protein, an HIF α subunit protein and a putative modulator compound under conditions where the VHL protein and the HIF α subunit protein, in the absence of modulator, are capable of forming a complex; and
   b) measuring the degree of inhibition of complex formation caused by said modulator compound.

2. The assay according to claim 1 in the form of a two-hybrid assay.

3. The assay according to claim 1 in the form of an immunoprecipitation.

4. The assay according to claim 1 wherein at least one of said proteins is labeled with a detectable label.

5. The assay according to claim 1 wherein at least one of said proteins is in the form of a fusion protein.

6. The assay according to claim 1 wherein the ubiquitylation of the HIF α subunit is determined.

7. The assay according to claim 1 wherein said VHL protein is human VHL (SEQ ID NO: 16) or a fragment thereof comprising at least residues 63–156.

8. The assay according to claim 1 wherein said HIF α subunit protein is human HIF α subunit protein (SEQ ID NO: 18) or a fragment thereof comprising at least residues 549–572.

9. An assay for a modulator which promotes VHL-HIF α subunit interaction, which assay comprises:
   a) bringing into contact an HIF α subunit protein and a putative modulator compound in the presence or absence of a VHL protein.
   b) providing a VHL protein where said protein is absent in step (a); and
   c) determining whether the VHL-HIF α subunit interaction has been promoted by the presence of the modulator.

10. The assay according to claim 1 wherein the degree of inhibition of complex formation is measured using an HIF response element to which the HIFα subunit protein is capable of binding and transcriptionally activating.

11. The assay according to claim 10 wherein said response element is operably linked to a reporter gene.

12. The assay according to claim 1 wherein the putative modulator compound is an inhibitor of the VHL-HIFα subunit interaction.

13. The assay according to claim 1 wherein inhibition of complex formation is indicative that said modulator compound is an inhibitor of VHL-HIFα subunit interaction.

14. The assay according to claim 1 wherein said modulator compound, when contacted with a cell exposed to hypoxia environment, inhibits the interaction between VHL and an HIFα subunit, thereby promoting angiogenesis and/or cellular survival.

15. A method of identifying an inhibitor of VHL-HIFα subunit interaction by performing the method of claim 1.

16. A method of inhibiting VHL-HIFα subunit interaction using an inhibitor identified by the method of claim 1.

* * * * *